US012758592B2

(12) United States Patent
Gueroui et al.

(10) Patent No.: US 12,758,592 B2
(45) Date of Patent: Oct. 13, 2026

(54) MAGNETIC BACTERIA, NON-THERAPEUTIC AND THERAPEUTIC USES THEREOF

(71) Applicants: PARIS SCIENCES ET LETTRES, Paris (FR); CENTRE NATIONAL DE LA RECHERCHE SCIENTIFIQUE, Paris (FR); SORBONNE UNIVERSITE, Paris (FR); MUSÉUM NATIONAL D'HISTOIRE NATURELLE (MNHN), Paris (FR)

(72) Inventors: Zoher Gueroui, Paris (FR); Mary Aubry, Paris (FR); Wei-An Wang, Pantin (FR); François Guyot, Paris (FR)

(73) Assignees: PARIS SCIENCES ET LETTRES, Paris (FR); CENTRE NATIONAL DE LA RECHERCHE SCIENTIFIQUE, Paris (FR); SORBONNE UNIVERSITE, Paris (FR); MUSEUM NATIONAL D'HISTOIRE NATURELLE (MNHN), Paris (FR)

( * ) Notice: Subject to any disclaimer, the term of this patent is extended or adjusted under 35 U.S.C. 154(b) by 987 days.

(21) Appl. No.: 17/629,524

(22) PCT Filed: Jul. 24, 2020

(86) PCT No.: PCT/EP2020/070984
§ 371 (c)(1),
(2) Date: Jan. 24, 2022

(87) PCT Pub. No.: WO2021/013998
PCT Pub. Date: Jan. 28, 2021

(65) Prior Publication Data

US 2022/0257671 A1 Aug. 18, 2022

(30) Foreign Application Priority Data

Jul. 24, 2019 (EP) .................................... 19188019

(51) Int. Cl.
*A61K 35/74* (2015.01)
*C07K 14/195* (2006.01)
*C12N 1/20* (2006.01)

(52) U.S. Cl.
CPC ............ *A61K 35/74* (2013.01); *C07K 14/195* (2013.01); *C12N 1/20* (2013.01)

(58) Field of Classification Search
CPC ......... A61K 35/74; C07K 14/195; C12N 1/20
See application file for complete search history.

(56) References Cited

U.S. PATENT DOCUMENTS

2021/0113484 A1* 4/2021 Drum .................... A61K 39/00

OTHER PUBLICATIONS

Matsumoto, Yuri, et al. "Engineering intracellular biomineralization and biosensing by a magnetic protein." Nature communications 6.1 (2015): 8721. (Year: 2015).*
García-Prieto, A., et al. "On the mineral core of ferritin-like proteins: structural and magnetic characterization." Nanoscale 8.2 (2016): 1088-1099 (Year: 2016).*
Garcia-Prieto supplemental data (Year: 2016).*
Tatur, Jana. "Structural and functional studies of the iron storage protein ferritin from Pyrococcus furiosus." (2007). (Year: 2007).*
R. P. Blakemore et al., "Isolation and Pure Culture of a Freshwater Magnetic Spirillum in Chemically Defined Medium"; Journal of Bacteriology, Nov. 1979; vol. 140, No. 2; 10 pgs.
Tal Danino et al.; "Programmable Probiotics for Detection of Cancer in Urine"; Science Translational Medicine; vol. 7; May 27, 2015; 28 pgs.
Remi Ducasse et al.; "Programmed Self-Assembly of a Biochemical and Magnetic Scaffold to Trigger and Manipulate Microtubule Structures"; Scientific Reports; vol. 7, Sep. 12, 2017; 11 pgs.
Quajdi Felfoul et al.; "Magneto-aerotactic bacteria deliver drug-containing nanoliposomes to tumour hypoxic regions"; Nature Nanotechnology; vol. 11; Nov. 2016; 17 pgs.
Michael Florea et al.; "Engineering control of bacterial cellulose production using a genetic toolkit and a new cellulose-producing strain"; Proceedings of the National Academy of Sciences of the United States of America; May 31, 2016; 10 pgs.
Richard B. Frankel et al.; "Magnetotaxis and magnetic particles in bacteria"; Hyperfine Interactions; 1994; 8 pgs.
A. Garcia-Prieto et al.; "On the mineral core of ferritin-like proteins: a structural and magnetic characterization"; Nanoscale; vol. 8; Oct. 9, 2015; 43 pgs.
David S. Glass et al.; "A Synthetic Bacterial Cell-Cell Adhesion Toolbox for Programming Multicellular Morphologies and Patterns"; Cell; vol. 174; Jul. 26, 2018; 27 pgs.
Philip J. Hill et al.; "Magnetic resonance imaging of tumors colonized with bacterial ferritin-expressing *Escherichia coli*"; PLOS ONE; vol. 6, Issue 10; Oct. 2011; 9 pgs.
Xueliang Liu et al.; "Engineering Genetically-Encoded Mineralization and Magnetism via Directed Evolution"; Scientific Reports; Nov. 29, 2016; 10 pgs.

(Continued)

*Primary Examiner* — Robert J Yamasaki
*Assistant Examiner* — Trevor Kane
(74) *Attorney, Agent, or Firm* — Maier & Maier, PLLC

(57) ABSTRACT

Recombinant, alive and metabolically active bacteria including a heterologous prokaryotic biomineralized ferritin. In particular, the inventors have shown that naturally non-magnetic *Escherichia coli* may be engineered to become magnetic by the expression and the biomineralization of the ferritin of *Pyrococcus furiosus*. Moreover, the inventors have shown that a fixed number of magnetic *E. coli* strains keep their magnetic properties through cell division by asymmetrical division. The inventors have also shown that magnetic bacteria according to the invention may be of use in both non-therapeutic and therapeutic uses, such as, e.g., the biosensing of target substance, the depollution of complex environments, the display of antibodies, nanobodies and antigens, the delivery of therapeutic substance to target cells, the targeting and infection of target cells.

14 Claims, 15 Drawing Sheets

Specification includes a Sequence Listing.

(56) References Cited

OTHER PUBLICATIONS

Yuri Matsumoto et al.; "Engineering intracellular biomineralization and biosensing by a magnetic protein"; Nature Communications; Nov. 2, 2015; 10 pgs.
Keiji Nishida et al.; "Induction of biogenic magnetization and redox control by a component of the target of rapamycin complex 1 signaling pathway"; PLOS Biology; vol. 10, Issue 2; Feb. 2012; 10 pgs.
Arthur Prindle et al.; "Sensing array of radically coupled genetic biopixels"; Nature; vol. 481; Jul. 5, 2012; 13 pgs.
Pradeep Ramesh, et al.; "Ultraparamagnetic Cells Formed through Intracellular Oxidation and Chelation of Paramagnetic Iron"; Angewandte Chemie International Edition; 2018; 7 pgs.
Dirk Schüler et al.; "Dynamics of iron uptake and Fe3O4 biomineralization during aerobic and microaerobic growth of Magnetospirillum gryphiswaldense"; Journal of Bacteriology; Jan. 1998; 4 pgs.
Justin L. Sonnenburg; "Synthetic biology may lead to the creation of smart microbes that can detect and treat disease"; Nature; vol. 518; Feb. 26, 2015; 1 pg.
Morgan M. Stanton et al.; "Pushing Bacterial Biohybrids to In Vivo Applications"; Trends in Biotechnology; Cell Press Reviews; vol. 35, No. 10; Oct. 2017; 4 pgs.
Jana Tatur, et al.; "The Dinuclear Iron-Oxo Ferroxidase Center of Pyrococcus Furiosus Ferritin Is a Stable Prosthetic Group With Unexpectedly High Reduction Potentials"; FEBS Letters; 2005; 4 pgs.
Jana Tatur et al.; "A highly thermostable ferritin from the hyperthermophilic archaeal anaerobe *Pyrococcus furiosus*"; Extremophiles; 2006; 10 pgs.
Zhantong Wang et al.; "Functional ferritin nanoparticles for biomedical applications"; Frontiers of Chemical Science Engineering; Dec. 2017; 27 pgs.

* cited by examiner

MAGNETIC BACTERIA, NON-THERAPEUTIC AND THERAPEUTIC USES THEREOF

FIELD

The present invention relates to recombinant, alive and metabolically active bacteria comprising a heterologous prokaryotic biomineralized ferritin. In particular, naturally non-magnetic *Escherichia coli* may be engineered to become magnetic by the expression and the biomineralization of the ferritin of *Pyrococcus furiosus*. Non-therapeutic and therapeutic uses may take advantage of the magnetic properties of said magnetic bacteria.

BACKGROUND

Recent progresses in synthetic biology showed how reprogrammed microbes could serve as in vivo whole-cell biosensors, as programmable delivery vehicles for therapeutic, or as diagnostic agents that could in the future be designed to address biomedical issues, such as, e.g., the treatment of yet incurable or difficult-to-treat diseases, such as cancer and infections, microbiome engineering (Danino, T. et al. Programmable probiotics for detection of cancer in urine. *Sci. Transl. Med.* 7, (2015); Sonnenburg, J. L. Synthetic biology may lead to the creation of smart microbes that can detect and treat disease. *Nature* 518, s10 (2015)).

However, several issues limit the use of microbes to solve technological problems including the spatial dissemination of the bacteria that drive to ineffective action, to biosafety issues, or to the lack of spatial controls. One solution to overcome such limitations could be the use of magnetic bacteria that are amenable to be directed in space and that conserve their biochemical activity.

Using magnetism as a physical property to monitor or control biological processes has been envisioned in the art. Magnetic sorting of colloidal particles, manipulations of biomolecules, magnetic resonance imaging, or magnetic hyperthermia, are examples of the many applications based on the use of magnetic nanoparticles with biological systems or with miniaturized devices (magnetic digital microfluidics). In this context, being able to engineer magnetic bacteria might provide a unique setting beyond the state of the art. Obtaining magnetic bacteria permit to combine two features: programmability of microbes and spatiotemporal control mediated by magnetic forces. Most organisms are simply diamagnetic and have no specific magnetic properties. On the other hand, magnetotactic bacteria are among the few living systems known to exploit magnetism. However, the biogenesis of the magnetosome involves complex interconnected processes, including magnetosome vesicle formation, iron uptake by the cell, iron transport into the vesicle, controlled $Fe_3O_4$ biomineralization, as well as the large-scale alignment of the magnetosomes by cytoskeleton fibers. Moreover, magnetotactic bacteria are fastidious microorganisms, as they are slow to grow and difficult to manipulate genetically.

In the area of whole-cell biosensors and bacteria diagnostics, monitoring toxins, pollutants, traces of chemicals, hormones, phages and/or pathogenic bacteria accurately and rapidly is an important task in the field of environment and health care. Programmed microbes could serve as in vivo whole-cell biosensors as tools for reporting on environmental changes and detecting specific molecules, such as small molecules produced by specific living pathogenic bacteria or a pollutant. In contrast to enzymes-based detector, whole cells are an excellent alternative since they have the benefit of low cost and improved stability comparing to enzymes or other proteins. Iterative steps of purification required could be avoided. Cells can be massively produced through a simple cell culturing step and the necessary cofactors are already present inside them. Moreover, microbes are easy to manipulate and have better stability under harsh environments. However, detecting such whole-cell biosensors in a complex environment or in the context of diagnostic assay remains difficult. Being able to selectively concentrate or sort bacterial biosensors could improve the detection and biosensor performance.

Regarding the possibility to spatially manipulate bacteria using magnetic field, 3 main strategies are currently developed, namely, magnetic biohybrids, magnetotactic bacteria (MTBs) and biomineralization of microorganisms, such as yeast and bacteria, to obtain magnetic properties.

Magnetic biohybrids have been envisioned on the basis of harnessing bacterial motility to power artificial cargos. Bacteria attached to micro- or nanoparticles are some of the best-studied bacterial biohybrid systems (Stanton, M. M. & Sánchez, S. Pushing Bacterial Biohybrids to In Vivo Applications. *Trends Biotechnol.* 35, 910-913 (2017)). Bacteria adhere to the particle and carry it while swimming, creating an effective cargo delivery system. Magnetic particles can be targeted to bacterial surfaces for guided swimming with an external magnetic source. For instance, *Salmonella typhimurium* bacteria were bound to microparticles that targeted tumor cell lysates. In addition, magnetotatic *Magnetococcus marinus* (MC-1) bacteria were used to carry drug-loaded nanoliposomes and were guided in a unified direction through a tumor in a mouse (Felfoul, O. et al. Magneto-aerotactic bacteria deliver drug-containing nanoliposomes to tumour hypoxic regions. *Nat. Nanotechnol.* 11, 941-947 (2016)). The limitation of these approaches relies on the conjugation of synthetic cargos to living bacteria, which could be invasive and limit their use in terms of applications. However, biocompatibility issues could arise from the use of synthetic cargos. In addition, such bioconjugation of bacteria and cargos require numerous iterative steps.

Among the few living systems known to exploit magnetism, magnetotactic bacteria use their unique intracellular organelles, the magnetosomes, to swim along the Earth's magnetic field (Frankel, R. B. & Bazylinski, D. A. Magnetotaxis and magnetic particles in bacteria. *Hyperfine Interact.* 90, 135-142 (1994)). The biogenesis of the magnetosome involves complex interconnected processes, including magnetosome vesicle formation, iron uptake by the cell, iron transport into the vesicle, controlled $Fe_3O_4$ (or $Fe_3S4$) biomineralization, as well as the large-scale alignment of the magnetosomes by cytoskeleton fibers along the bacterial long axis (Schüler, D. & Baeuerlein, E. Dynamics of iron uptake and $Fe_3O_4$ biomineralization during aerobic and microaerobic growth of *Magnetospirillum gryphiswaldense. J. Bacteriol.* 180, 159-62 (1998)). However, magnetotactic bacteria are fastidious microorganisms, as they are slow to grow and are difficult to manipulate (Blakemore, R. P., Maratea, D. & Wolfe, R. S. Isolation and pure culture of a freshwater magnetic spirillum in chemically defined medium. *J. Bacteriol.* 140, 720-9 (1979)). For instance, their genome is complicated (the nanocrystal synthesis requires about hundred genes), and the magnetosomes are not directly biocompatible. It is difficult to modify genetically the magnetosomes in order to confer them new properties. That is why biological or medical applications with magnetotactic bacteria are quite difficult.

To date, four studies had described the biomineralization of microbes to obtain magnetic properties. A first study has reported the biomineralization of yeast cells and identifies redox pathway as key for inducing paramagnetic properties (Nishida, K. & Silver, P. A. Induction of biogenic magnetization and redox control by a component of the target of rapamycin complex 1 signaling pathway. *PLoS Biol.* (2012). doi:10.1371/journal.pbio. 1001269). Two other studies aimed to use directed evolution to generate a library of ferritin mutants using yeast and bacteria with the goal to enlarge iron storage capacity (Liu, X. et al. Engineering Genetically-Encoded Mineralization and Magnetism via Directed Evolution. *Sci. Rep.* (2016). doi:10.1038/srep38019; Matsumoto, Y., Chen, R., Anikeeva, P. & Jasanoff, A. Engineering intracellular biomineralization and biosensing by a magnetic protein. *Nat. Commun.* 6, 8721 (2015)). The last report described the biomineralization of bacteria expressing magnetite nucleating peptide (M6A) leading to obtain paramagnetic bacteria (Ramesh, P. et al. Ultraparamagnetic Cells Formed through Intracellular Oxidation and Chelation of Paramagnetic Iron. *Angewandte Chemie—International Edition* (2018). doi:10.1002/anie.201805042). While some of these methods explore the possibility to magnetically sort the bacteria, they did not achieve spatial control of bacterial concentration. Importantly, these studies did not report that the resulting mineralized bacteria can be biochemically active, sustain cell division processes, or transmit and maintain their magnetic properties, which are the three main requirements for using magnetic bacteria as tools in biotechnology. In particular, obtaining magnetized bacteria that can sustain cell division is of primary importance for basic understanding and to envision applications requiring magnetic manipulations of bacteria in a complex environment after hours or days.

As already mentioned, concentration and/or sorting of bacteria from a complex environment could improve the detection and performance of microorganisms used as biosensors for diagnostic or monitoring purposes.

Conventional concentration techniques are based on centrifugation, membrane filtering, or capturing by functionalized magnetic beads. In the context of microfluidic diagnostic platforms, the three main concepts for chip-based bacteria concentration are physical trapping, functionalized particles, and electro-kinetic techniques. Physical traps for bacteria are fabricated by shallow channels or arrays of microbeads. Antibody-coated particles have been used to selectively bind to the target species. These particles are trapped in microchannels by physical barriers or magnetic fields. The capture efficiency strongly depends on the quality of the coatings and proper mixing of particles and analytes. Di-electrophoresis has widely been used for preconcentration and separation of cells and bacteria.

Current approaches for detecting specific bacterial strains, such as, e.g. pathogenic bacteria, are using common principles of biochemistry and/or molecular biology.

One approach involves culture-based methods. These methods are based on culture methods, and biochemical detection. They are time-consuming, since they can take several days to confirm the presence of a pathogen, and expensive. The quantitative data are difficult to extract because of the enrichment steps of the medium.

Another approach consists in Polymerase Chain Reaction (PCR) or real time PCR (qPCR) detection, based on DNA recognition. Databases list the genes of pathogenic species. To investigate the presence of a pathogen in a sample, the medium is treated to lyse the bacteria, and a PCR is launched on the DNA present in the sample. If there is a pathogen, the amplified gene is detected by fluorescence (with specific dyes). Even if it is faster (few hours) than the traditional methods, the major drawback of PCR is the fact that it cannot discriminate dead and alive bacteria. There could be an overestimation of the concentration of a pathogen in a sample due to a contamination by the DNA of dead cells (that can last long in the medium after cell death). Moreover, with PCR, we can detect one pathogen at a time. RT PCR is a method that can detect only viable cells, but requires an enrichment of the medium. False positive/negative occurs (interferences with the sample), so precise controls are essential.

Another approach encompasses the recognition of pathogen by antibody/antigen complex. ELISA tests are one exemplary embodiment. Specific antigens of pathogenic bacteria can be recognized by monoclonal antibodies. The antibodies can then be fused with an enzyme that can react to reveal the presence of antigens. This method is simple, but has a low level of detection. Plus, the enzymatic reaction can be dependent of pH or temperature conditions.

A still further approach involves magneto-immunocapture. Several companies are currently developing technologies using magnetic nanoparticles in order to reduce amount/cost/time of pathogens capture using antibody. However, this approach is not very selective, in that it also detects dead bacteria and is dependent on the antibody efficiency.

Finally, other approaches comprise the identification by mass spectrometry, which is expensive, as it requires prior PCR steps and whole genome sequencing, which remains expensive and require dealing with a large amount of sequencing data.

Therefore, there is a need to provide the state of the art with a mean for easily, specifically and efficiently detecting microorganisms, such as bacteria and more particularly alive pathogenic bacteria, in a given environment.

There is a need to provide the state of the art with a biosensor device, which can be useful to detect small molecule, such as pollutant, in a given environment, in particular a complex environment.

There is a need to provide the state of the art with a drug delivery system that is performant, safe and easy to handle.

SUMMARY

One aspect of the invention relates to a recombinant, alive and metabolically active bacterium comprising a heterologous prokaryotic biomineralized ferritin. In certain embodiments, said bacterium has magnetic properties. In some embodiments, said bacterium is of the genus *Escherichia*, preferably of the species *E. coli*. In some embodiments, said prokaryotic ferritin is originating from an archaeon, preferably an archaeon of the genus *Pyrococcus*, more preferably of the species *Pyrococcus furiosus*.

Another aspect of the invention relates to a method for producing recombinant, alive and metabolically active bacteria, in particular bacteria having magnetic properties, comprising a heterologous prokaryotic biomineralized ferritin, comprising the steps of:

a) providing recombinant bacteria expressing a heterologous prokaryotic ferritin;
b) contacting said recombinant bacteria with a medium comprising $Fe^{2+}$, so as to allow biomineralization;
c) collecting alive and metabolically active bacteria comprising the biomineralized ferritins.

In some embodiments, the final concentration of $Fe^{2+}$ in step b) is from about 0.5 mM to about 10 mM, more preferably from about 1 mM to about 5 mM.

One aspect of the invention pertains to a magnetic nanocage comprising biomineralized ferritins from *Pyrococcus furiosus.*

In another aspect, the invention relates to the use of a recombinant bacterium according to the invention for its magnetic properties. In some embodiments, the recombinant bacterium according to the invention is of use as a biosensor, in particular for the detection and/or the capture of one or more target chemical substance(s) and/or one or more organism(s) in a complex environment. In certain embodiments, the bacterium is for use for the surface display of a ligand, preferably an antibody, a nanobody, and/or an antigen. In some embodiments, the bacterium is for use for the production of functionalized magnetic nanocages comprising biomineralized ferritins from *Pyrococcus furiosus.*

Another aspect of the invention relates to a recombinant bacterium according to the invention for use in therapy. In certain embodiments, the recombinant bacterium is for use as a molecule delivery system. In some embodiments, the recombinant bacterium is for use for the therapeutic diagnostic of a disorder. In some embodiments, the recombinant bacterium is for use for the surface display of a protein of interest that recognizes and/or penetrates a target cell. In certain embodiments, the target cell is a mammal target cell, preferably a human target cell.

BRIEF DESCRIPTION OF THE DRAWINGS

FIG. 1B represents an enlargement of the squared region depicted in FIG. 1A. Scale bars, 200 nm (A) and 50 nm (B).

DEFINITIONS

Figure 1A:
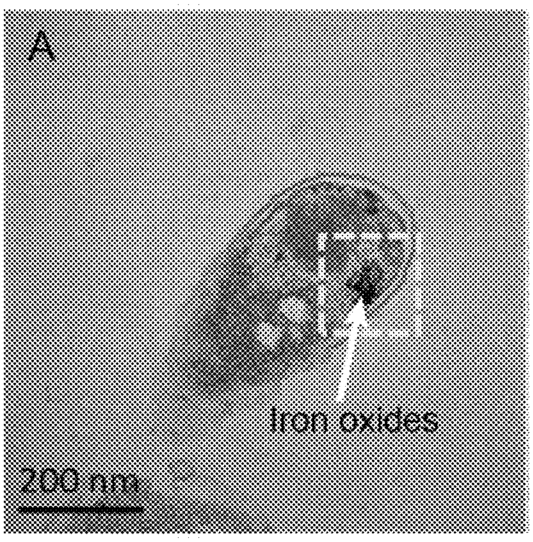
FIGS. 1A and 1B represent micrographs of high resolution TEM image of a cross sectioned mineralized *E. coli* mCherry strain.

In the present invention, the following terms have the following meanings:

"About" preceding a figure encompasses plus or minus 10%, or less, of the value of said figure. It is to be understood that the value to which the term "about" refers is itself also specifically, and preferably, disclosed.

"Recombinant" refers to a bacterium that is produced by genetic engineering.

"Alive" or "live" refers to a microorganism, in particular a bacterium, capable of performing growth and division within a suitable environment.

"Metabolically active" refers to a microorganism, in particular a bacterium, capable of performing the uptake and/or the synthesis of essential nutrients to achieve growth and division in a suitable environment. In addition, the bacteria can achieve essential functions, such as the heterologous synthesis of proteins that remain functional.

"Magnetic bacterium" refers to a bacterium that has magnetic properties, such as, e.g., paramagnetic or superparamagnetic properties. As a consequence, the application of a gradient of magnetic field, using a magnet for instance, results in generating magnetic forces that are sufficient to attract, concentrate, localize, and/or sort magnetic bacteria.

"Biomineralization" refers to the process by which a living organism, in particular a bacterium, produces solid phases such as minerals. Illustratively, iron biomineralization of bacteria results in the formation of iron oxides. By extension, a "biomineralized ferritin" refers to a ferritin that sequesters and catalyzes $Fe^{2+}$ (iron (II)) into $Fe^{3+}$ (iron (III)) and thus forms iron oxide dense phases within its cavity inside the bacteria.

"Transmission of magnetic properties through cell division" refers to the conservation of magnetic properties through division of a bacterium due to the asymmetrical transmission of iron oxides ferritin-enriched bodies to daughter cells. As a consequence, a fixed number of bacteria conserve its magnetic properties despite the cell division processes.

"Nanocage" refers to a 3D-structured hollow self-assembly of protein subunits at the nanometer scale, in particular of 24 ferritins (or 24 ferritin subunits, also refer to a 24-mer of ferritin). By extension, a "nanocage" according to the instant invention refers to the assembly of ferritin as a nanoparticle.

"Heterologous" refers to a prokaryotic ferritin that is originating from another species than the species of the bacterium comprising said ferritin.

"Complex environment" refers to an environment comprising a combination of organic and/or non-organic substances, such as e.g. solvent, trace elements, nutrients, polymers, microorganisms, cells, etc.

"Programmed bacterium" refers to a bacterium that is engineered to perform a function of interest. Illustratively, a bacterium may be programmed to sense a target molecule and emit a detectable signal upon sensing said target molecule.

"Concentration" or "concentrate" may refer to the action of locally accumulating a target of interest.

"Sorting" or "sort" refer to the action of separating targets sharing a given characteristic from a mixture of targets with distinct characteristics.

"Treating" or "treatment" or "alleviation" refers to both therapeutic treatment and prophylactic or preventative measures, wherein the object is to prevent or slow down (lessen) a disorder. Those in need of treatment include those already with said disorder as well as those prone to develop the disorder or those in whom the disorder is to be prevented. An individual is successfully "treated" for a disorder if, after receiving a therapeutic amount of the recombinant bacteria according to the present invention, the individual shows observable and/or measurable reduction in or absence of one or more of the symptoms associated with said disorder; reduced morbidity and mortality, and improvement in quality of life issues. The above parameters for assessing successful treatment and improvement in the disease are readily measurable by routine procedures familiar to physician or authorized personnel.

"Preventing" refers to keeping from happening, and/or lowering the chance of the onset of, at least one adverse effect or symptom of a disorder or condition associated with a deficiency in or absence of an organ, tissue or cell function.

"Therapeutic efficient amount" refers to the level or the amount of the active agent that is aimed at, without causing significant negative or adverse side effects to the target, (1) delaying or preventing the onset of a disorder, (2) slowing down or stopping the progression, aggravation, or deterioration of one or more symptoms of disorder; (3) bringing about ameliorations of the symptoms of a disorder, (4) reducing the severity or incidence of a disorder; or (5) curing a disorder. A therapeutic efficient amount may be administered prior to the onset of a disorder, for a prophylactic or preventive action. Alternatively, or additionally, the therapeutic efficient amount may be administered after the onset of a disorder, for a therapeutic action. In one embodiment, a therapeutic efficient amount of the composition is an amount that is effective in reducing at least one symptom of a disorder.

"Pharmaceutically acceptable vehicle" refers to a vehicle that does not produce any adverse, allergic or other unwanted reactions when administered to an animal individual, preferably a human individual. It includes any and all solvents, dispersion media, coatings, antibacterial and antifungal agents, isotonic and absorption delaying agents and the like. For human administration, preparations should meet sterility, pyrogenicity, general safety, quality and purity standards as required by regulatory Offices, such as, e.g. the FDA in the United States or the EMA in the European Union.

"Individual" is intended to refer to an animal individual, preferably a mammal individual, more preferably a human individual. Non-limitative non-human mammal individuals of interest may encompass pets, such as dogs, cats, rats, mice, rats, guinea pigs; animals of economic importance such as cattle, sheep, goats, horses, monkeys.

DETAILED DESCRIPTION

In recent years, academic knowledge has been acquired on ferritins. For example, Garcia-Prieto et al. (On the Mineral Core of Ferritin-Like Proteins: Structural and Magnetic Characterization. *Nanoscale,* 2016, vol. 8(2):1088-1099) reported recombinant *E. coli* strains comprising plasmids allowing the overproduction of ferritin proteins, i.e. ferritin from *E. coli* FtnA, bacterioferritin (Bfr) and ferritin from *Pyrococcus furiosus* (PfFtn), in a growth medium (LB) that is supplemented or not with 100 μM Fe(III)-citrate. Tatur and Hagen (The Dinuclear Iron-Oxo Ferroxidase Center of *Pyrococcus Furiosus* Ferritin Is a Stable Prosthetic Group With Unexpectedly High Reduction Potentials. *FEBS Letters,* 2005, vol. 579(21):4729-4732) and Tatur et al (A highly thermostable ferritin from the hyperthermophilic archaeal anaerobe *Pyrococcus furiosus. Extremophiles,* 2006, vol. 10(2): 139-148) both reported cloning and overproduction of the ferritin from *P. furiosus* in *E. coli*. Whereas non-mineralized cellular ferritin (apo-protein) has low amount of iron bound per ferritin subunit, extracted and isolated ferritin could further be mineralized in vitro in order to increase the amount of iron loaded per subunit. However, all of these recombinant bacteria were not reported as being magnetic bacteria, i.e., bacteria with magnetic properties.

Finally, Hill et al. (Magnetic Resonance Imaging of Tumors Colonized With Bacterial Ferritin-Expressing *Escherichia Coli. PLOS One,* 2011, vol. 6(10):e25409) reported the cloning and overexpression of ferritin in an *E. coli* strain. The recombinant bacteria are grown in BHI culture medium supplemented with 150 μM ferrous-citrate.

The inventors have managed to synthetically induce magnetism in commonly used strains amenable for engineering and medical purpose such as *Escherichia coli*, which are easy-to-grow microbes and are at the foundation of numerous biotechnology industries.

This invention relates to a recombinant, alive and metabolically active bacterium comprising a heterologous prokaryotic biomineralized ferritin. The invention also relates to a recombinant, alive and metabolically active magnetic bacterium comprising a heterologous prokaryotic biomineralized ferritin.

In some embodiments, the bacterium according to the instant invention is exclusively a non-pathogenic bacterium. As used herein, the term "non-pathogenic" refers to a bacterium that does not harm or cause an infection in a target vegetal or animal, in particular a mammal animal, more preferably a human.

In some embodiments, the bacterium according to the invention may be an attenuated pathogenic bacterium. As used herein, the expression "attenuated pathogenic" refers to a bacterium that has a reduced virulence, as compared to a non-attenuated pathogen. Non-limited examples of attenuated pathogenic bacteria may comprise attenuated bacteria of the genus *Pseudomonas*, preferably *P. aeruginosa*; of the genus *Listeria*, preferably *L. monocytogenes.*

In some embodiments, the bacterium is a Gram-negative bacterium. In practice, the Gram coloration may be performed according to the methods well described in the state of the art. In some embodiments, the bacterium is from the family of Enterobacteriaceae.

In some embodiments, said bacterium is of the genus *Escherichia*, preferably of the species *E. coli.*

As acknowledged in the state in the art, *E. coli* is a bacterial strain that is naturally found in the intestinal flora of many mammal individuals, in particular human individuals.

In some embodiments, the bacterium of the species *E. coli* is selected in the non-limiting group comprising the SIGMA-ALDRICH® BL21(DE3) strain, the THERMOFISHER® DH5-Alpha strain, the THERMOFISHER®

DH10B strain, the THERMOFISHER® INV110 strain, the THERMOFISHER® MG1655 strain, the Rosetta® strain and the THERMOFISHER® TOP10 strain.

In practice, the SIGMA-ALDRICH® BL21(DE3) strain has the following genotype: $F^-$ ompT $hsdS_B$ ($r_B^-$ $m_B^-$) gal dcm (DE3); the THERMOFISHER® DH5-Alpha strain has the following genotype: $F^-$ φ80lacZΔM15 Δ(lacZYA-argF) U169 recA1 endA1 hsdR17($r_K^-$, $m_K^+$) phoA supE44$\lambda^-$ thi-1 gyrA96 relA1; the THERMOFISHER® DH10B strain has the following genotype: $F^-$ mcrA Δ(mrr-hsdRMS-mcrBC) φ80lacZΔM15 ΔlacX74 recA1 endA1 araD139 Δ(ara-leu) 7697 galU galK $\lambda^-$ rpsL($Str^R$)nupG; the THERMOFISHER® INV110 strain has the following genotype: F' [traD36proAB $lacI^q$ lacZΔM15] rpsL ($Str^R$) thr leu endA thi-1 lacY galK galT ara tonA tsx dam dcm supE44 Δ(lac-proAB) Δ(mcrC-mrr)102::Tn10($Tet^R$); the THERMOFISHER® Mach1 strain has the following genotype: $F^-$ φ80lacZΔM15 ΔlacX74 hsdR($r_K^-$, $m_K^+$) ΔreccA1398 endA1 tonA; the MG1655 strain has the following genotype: $F^-$ $\lambda^-$ $ilvG^-$ rfb-50 rph-1; the Rosetta® strain has the following genotype: $F^-$ ompT $hsdS_B$($r_B^-$ $m_B^-$) gal dcm (DE3) pRARE ($Cam^R$); the THERMOFISHER® TOP10 strain has the following genotype: $F^-$ mcrA Δ(mrr-hsdRMS-mcrBC) φ80lacZΔM15 ΔlacX74 recA1 araD139 Δ(ara-leu) 7697 galU galK $\lambda^-$ rpsL($Str^R$) endA1 nupG.

The "alive" characteristic of a bacterium according to the invention may be assessed by any suitable method available in the state of the art. In practice. the bacterium according to the invention may be contacted with a culture medium comprising the essential nutrients for allowing bacterial growth and/or division, in condition of temperature and $O_2$ known to support growth. Illustratively, growth and/or division of the bacterium may be assessed by measuring the optical density, e.g. at 600 nm. An increase of the optical density at 600 nm over the course of the culture is indicative of the growth and/or division of the bacterium in the defined culture conditions. Another method to assess growth and/or division may be performed by measuring the number of "colony forming unit" (CFU) during the course of the culture. An increase of the CFU over the course of the culture is indicative of the growth and/or division of the bacterium in the defined culture conditions. In some embodiments, an observation of the culture by optical microscopy may be performed to assess the ability of the bacteria to divide.

In some embodiments, the bacterium according to the invention transmits its magnetic properties through cell division.

The conservation of magnetic properties through division of a bacterium according to the invention is due to the asymmetrical transmission of iron oxides ferritin-enriched bodies to daughter cells. The capacity to transmit the magnetic properties of a bacterium according to the invention may be assessed using a combination of optical density measurements, live microscopy observations, and magnetophoresis (method used to quantify the motion of bacteria within a gradient of magnetic field).

The activity of the metabolism of the bacterium according to the instant invention may be assessed by measuring the decrease of the concentration of one or more essential nutrient comprised in the culture medium. Inversely, the activity of the metabolism of the bacterium according to the instant invention may be assessed by measuring the increase of the level of a specific metabolite synthesized by said bacterium. In practice, radiolabeled nutrients may be fed to the bacterium by the mean of the culture medium. A decrease of the concentration of the radiolabeled nutrient in the culture medium during the course of the culture is indicative of an uptake of said nutrient by the bacterium, and hence is indicative of an active metabolism. Illustratively, samples of the bacterial culture may be collected during the course of the culture, and a mass spectrometry analysis may be performed to measure levels of a specific metabolite.

As used herein, an "increase" refers to a level superior to a reference level. Illustratively, a reference level may be measured at T0 and subsequent levels may be measured at Tn (n being different from 0), during the time course of the culture. In other words, an increase refers to a level at Tn that is superior than the level at T0. As used herein, the term "superior" refers to a ratio level Tn/level TO strictly superior to 1, in particular superior to 1.1, preferably superior to 1.25, more preferably superior to 1.5. Within the scope of the instant invention, the expression "strictly superior to 1" encompasses 1.1, 1.2, 1.25, 1.3, 1.4, 1.5, 1.6, 1.7, 1.8, 1.9, 2, 2.5, 3, 3.5, 4, 4.5, 5, 7.5, 10, 12.5, 15, 17.5, 20, 25, 30, 40, 50, 75, 100, 125, 150, 175, 200, 225, 250, 275, 300, 500, 750, 1,000, 1,500.

As used herein, a "decrease" refers to a level inferior to a reference level. Illustratively, a reference level may be measured at TO and a subsequent level may be measured at Tn (n being different from 0), during the time course of the culture. In other words, a decrease refers to a level at Tn that is inferior than the level at T0. As used herein, the term "inferior" refers to a ratio level Tn/level T) strictly inferior to 1, in particular inferior to 0.9, preferably inferior to 0.75, more preferably inferior to 0.5. Within the scope of the instant invention, the expression "strictly inferior to 1" encompasses 0.9, 0.85, 0.8, 0.75, 0.7, 0.65, 0.6, 0.55, 0.5, 0.4, 0.3, 0.2, 0.1, 0.075, 0.05, 0.025, 0.01, 0.0075, 0.005, 0.0025, 0.001.

It is understood that a suitable culture medium for use according to the invention may be an aqueous medium that may include a combination of substances such as one or more salts, carbon sources, amino acid sources, minerals. reducing agents, buffering agents.

In practice, non-limitative examples of suitable culture media for bacterial growth encompass LB broth, Terrific broth and M9 minimal medium.

Commercially available culture media may be purchased from e.g. SIGMA-ALDRICH®, THERMOFISHER®, to name a few companies.

In some embodiments, the bacterium according to the instant invention may comprise one or more genomic point mutation(s) that increase the magnetic properties, in particular the paramagnetic properties. In certain embodiments, the point mutation may be localized in the genes involved in the iron uptake.

In some embodiments, the bacterium according to the instant invention may be a programmed bacterium. In practice. a programmed bacterium according to the invention may be engineered as to performed one or more function(s) of interest. Illustratively, a bacterium may be programmed to sense a target molecule and emit a detectable signal upon sensing said target molecule.

In some embodiments, the signal may be selected in the group of a change in optical density, the emission of fluorescence, luminescence, an increase in an enzymatic activity, a change in magnetic properties, and the like. Illustratively, the fluorescence may be any fluorescence from a far-red fluorescence, a red fluorescence, a yellow fluorescence, a green fluorescence, or a blue fluorescence.

In some embodiments, said prokaryotic ferritin is originating from an archaeon, preferably an archaeon of the genus *Pyrococcus*, more preferably of the species *Pyrococcus furiosus*.

In some embodiments, the ferritin from *P. furiosus* is represented by an amino acid sequence having at least 75% amino acid sequence identity to SEQ ID NO: 1. Within the scope of the invention, the expression "at least 75% amino acid identity" encompasses 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% amino acid identity.

In some embodiments, the ferritin from *P. furiosus* is represented by an amino acid sequence having at least 80%, preferably at least 90%, more preferably at least 95% amino acid sequence identity to SEQ ID NO: 1. In some embodiments, the ferritin from *P. furiosus* is represented by amino acid sequence SEQ ID NO: 1.

As used herein, the ferritin from *P. furiosus* (strain DSM 3638) represented by the 174 amino acid sequence SEQ ID NO: 1 refers to a protein with the GenBank accession number AAL80866.1.

The term "identity", when used in a relationship between the sequences of two or more polypeptides or of two or more nucleic acid molecules, refers to the degree of sequence relatedness between polypeptides or nucleic acid molecules, as determined by the number of matches between strings of two or more amino acid or nucleotide residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity. In some embodiments, the term identity is measured over the entire length of the sequence to which it refers.

Illustratively, the amino acid identity percentage may also be determined using the CLUSTAL W software (version 1.83) the parameters being set as follows:

for slow/accurate alignments: (1) Gap Open Penalty: 10.00; (2) Gap Extension Penalty:0.1; (3) Protein weight matrix: BLOSUM;

for fast/approximate alignments: (5) Gap penalty: 3; (6) K-tuple (word) size: 1; (7) No. of top diagonals: 5; (8) Window size: 5; (9) Scoring Method: PERCENT.

In some embodiments, said prokaryotic ferritin may be advantageously fused to a label domain. In certain embodiments, the label domain may be a tag, for the ease of purification of ferritin; a fluorescent domain, for the ease of detection of a biomineralized ferritin or a bacterium comprising a biomineralized ferritin. Non-limiting examples of tags suitable for the invention may be selected in a group comprising a FLAG-tag, His-tag, GST-tag, MBP-tag, SUMO-tag, Halo-Tag, Snap-Tag and a combination thereof. Non-limiting examples of fluorescent domains suitable for the invention may be selected in a group comprising mCherry, GFP, EGFP, mRaspberry, mVenus, mTurquoise, Emerald (EmGFP), EBFP, Azurite, ECFP, mECFP, Cerulean, EYFP, mCitrine, mOrange, DsRed, mTangerine, mRuby, mApple, mPlum.

In practice, a biomineralized ferritin according to the invention relates to a ferritin that sequesters and catalyzes iron (II) into iron (III) and thus forms iron oxide dense phases within its cavity inside the bacteria. Illustratively, upon the uptake of iron by the bacterium, the confinement of iron within the ferritin cavity leads to the formation of iron oxides within ferritins in vivo, i.e. inside the bacterium.

Another aspect of the invention further relates to a pharmaceutical composition comprising the recombinant bacterium according to the invention and a pharmaceutically acceptable vehicle. In some embodiments, a suitable pharmaceutically acceptable vehicle may include any and all conventional solvents, dispersion media, fillers, solid carriers, aqueous solutions, coatings, antibacterial and antifungal agents, isotonic and absorption delaying agents, and the like. In certain embodiments, suitable pharmaceutically acceptable vehicles may include, water, saline, phosphate buffered saline, dextrose, glycerol, ethanol and a mixture thereof. In some embodiments, the pharmaceutical composition according to the invention may be administered in by any suitable route, including the oral route, the topical route.

In certain embodiments, the bacterium according to the invention has magnetic properties. As understood herein, the recombinant, alive and metabolically active bacterium comprising a heterologous prokaryotic biomineralized ferritin is a magnetic bacterium. In other words, the magnetic bacterium may be attracted by a magnetic field, e.g. by the mean of a millimeter-sized magnet (NdFeB) generating a magnetic gradient of from about 0.1 to about $10^4$ $T \cdot m^{-1}$ when positioned at several hundreds of micrometer (μm) from the bacterium.

Within the scope of the invention, the expression "from about 0.1 to about $10^4$ $T \cdot m^{-1}$" encompasses 0.1, 0.5, 1, 2, 3, 4, 5, 6, 7, 8, 9, $10^1$, $5\times10^1$, $10^2$, $5\times10^2$, $10^3$, $5\times10^3$ and $10^4$ $T \cdot m^{-1}$.

Within the scope of the invention, the expression "several hundreds of micrometer" encompasses at least 200 μm, 300 μm, 400 μm, 500 μm, 600 μm, 700 μm, 800 μm and 900 μm.

One aspect of the invention relates to a method for producing recombinant, alive and metabolically active bacteria, in particular bacteria having magnetic properties, comprising a heterologous prokaryotic biomineralized ferritin, comprising the steps of:

a) providing recombinant bacteria expressing a heterologous prokaryotic ferritin;
b) contacting said recombinant bacteria with a medium comprising $Fe^{2+}$, so as to allow biomineralization;
c) collecting alive and metabolically active bacteria comprising the biomineralized ferritin.

Within the scope of the instant invention, the term "contacting" refers to mixing two entities in the same container. The term "contacting" is therefore equivalent to the expression "bringing into contact".

In practice, the bacterium according to the invention being recombinant, it comprises a heterologous nucleic acid encoding a prokaryotic ferritin.

In some embodiments, the collected bacterium at step c) may further be characterized by a capacity to transmit its magnetic properties through cell division.

In some embodiments, said heterologous nucleic acid is extra-genomic.

In certain embodiments, the nucleic acid encodes a ferritin from an archaeon of the genus *Pyrococcus*, more preferably of the species *Pyrococcus furiosus*.

In some embodiments, the nucleic acid encoding the ferritin from *P. furiosus* is represented by a nucleic acid sequence having at least 75% nucleic acid sequence identity to SEQ ID NO: 2. Within the scope of the invention, the expression "at least 75% nucleic acid identity" encompasses 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% nucleic acid identity.

In some embodiments, the nucleic acid encoding the ferritin from *P. furiosus* is represented by a nucleic acid sequence having at least 80%, preferably at least 90%, more preferably at least 95% nucleic acid sequence identity to SEQ ID NO: 2. In some embodiments, the nucleic acid encoding the ferritin from *P. furiosus* is represented by the nucleic acid sequence SEQ ID NO: 2.

As used herein, the ferritin from *P. furiosus* (strain DSM 3638) represented by the 525 bp nucleic acid sequence SEQ ID NO: 2 refers to a nucleic acid with the GenBank accession number NC_003413.

The level of identity of 2 nucleic acid sequences may be performed by using any one of the known algorithms available from the state of the art.

Illustratively, the nucleic acid identity percentage may be determined using the CLUSTAL W software (version 1.83) the parameters being set as follows:

for slow/accurate alignments: (1) Gap Open Penalty: 15; (2) Gap Extension Penalty: 6.66; (3) Weight matrix: IUB;

for fast/approximate alignments: (4) K-tuple (word) size: 2; (5) Gap Penalty: 5; (6) No. of top diagonals: 5; (7) Window size: 4; (8) Scoring Method: PERCENT.

Therefore, another aspect of the invention relates to a method for producing a recombinant, bacterium expressing a heterologous prokaryotic ferritin comprising the steps of:

a) contacting nucleic acids encoding a prokaryotic ferritin with competent bacteria;

b) transforming said competent bacteria with said nucleic acids;

c) selecting bacteria expressing the prokaryotic ferritin.

In practice, the nucleic acid encoding the prokaryotic ferritin is in the form of a plasmid, in particular resulting from the cloning of the prokaryotic ferritin gene into a vector. In some embodiments, non-limitative suitable vectors are pET vectors, pETduet vectors, pGBM vectors, pBAD vectors, pUC vectors. In some embodiments, the vector may also comprise a promoter that is inducible, in particular the promoter of the lacZ gene, the promoter of the trp gene or the promoter of the β-lactamase encoding gene. In practice, the vector comprises a nucleic acid encoding the resistance to an antibiotic, in particular, ampicillin, kanamycin, chloramphenicol, tetracycline, spectinomycin or streptomycin, for the ease of selection of the transformed bacterium.

In some embodiments, competent bacteria may be chemically competent cells, in particular calcium chloride treated bacteria. In some alternative embodiments, competent bacteria may be electrocompetent bacteria. In practice, chemically competent or electrocompetent bacteria may be purchased from THERMOFISHER® or SIGMA-ALDRICH®. For *E. coli* bacteria, a non-limitative list of commercial chemically competent bacteria encompasses SIGMA-ALDRICH® BL21(DE3), THERMOFISHER® DH10B, THERMOFISHER® DH5α, THERMOFISHER® Mach1, THERMOFISHER® TOP10, THERMOFISHER® INV110, SIG10. A non-limitative list of commercial *E. coli* electrocompetent bacteria encompasses THERMOFISHER® Mega DH10B TiR, THERMOFISHER® ElectroMAX DH5α, THERMOFISHER® One shot TOP10, SIGMA-ALDRICH® SIG10 MAX.

In some embodiments, step c) of selecting bacteria expressing the prokaryotic ferritin is performed by first selecting the bacteria that are resistant to the presence of an antibiotic. The expression of the prokaryotic ferritin may be assessed by any suitable method, in particular, the measure of the levels of the ferritin mRNAs, the measure of the levels of the ferritin protein, the measure of the activity of the ferritin protein.

In some embodiments, said heterologous nucleic acid is intra-genomic.

In practice, the insertion of the nucleic acid encoding the prokaryotic ferritin into the genome of the bacterium according to the invention may be achieved by recombination. In some embodiments, the recombination may be achieved by the mean of a bacteriophage. In practice, the process of insertion of a nucleic acid in the genome by recombination by the mean of a bacteriophage is referred to transduction. Non-limitative suitable phages for performing transduction may be e.g. phage P1 and phage λ.

Preparation of a recombinant bacterium expressing a heterologous prokaryotic ferritin may be achieved by complying with the methods and protocols known from the state of the art. Illustratively, for the steps of cloning, preparation of competent bacteria, preparation of lysate of phage, transformation or transduction, selection of transformed or transduced bacteria one may refer to the manufacturer's instructions, when commercial kits or materials are used, and/or alternatively refer to the protocols described by Maniatis et al. (Molecular cloning: a laboratory manual. Cold Spring Harbor Laboratory, 1982).

It is understood that the heterologous prokaryotic ferritin expressed by the recombinant bacteria may be subsequently biomineralized. As mentioned above, the biomineralization step consists in allowing the recombinant bacteria expressing a heterologous prokaryotic ferritin to uptake iron, allowing the ferritin to sequester $Fe^{2+}$ ions (also referred as to iron (II)) within its cavity, which leads to the in vivo formation of iron oxides within ferritins. In practice, the biomineralization step comprises contacting the recombinant bacteria expressing a heterologous prokaryotic ferritin with a medium comprising $Fe^{2+}$. In certain embodiments, the combination of bacteria expressing a heterologous prokaryotic ferritin with a medium comprising $Fe^{2+}$ is in the form of a suspension, in particular a bacterial suspension.

In some embodiments, the final concentration of $Fe^{2+}$ in step b) is from about 0.5 mM to about 10 mM, more preferably from about 1 mM to about 5 mM.

As used herein, the expression "from about 0.5 mM to about 10 mM" encompasses about 0.5 mM, 1.0 mM, 1.5 mM, 2.0 mM, 2.5 mM, 3.0 mM, 3.5 mM, 4.0 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM and 10.0 mM.

The inventors have observed that the bacterium according to the instant invention support relatively higher amounts of $Fe^{2+}$ in the culture medium, contrary to non-expressing ferritin bacteria. The inventors observed that relatively high amounts of $Fe^{2+}$ in the culture medium does not affect the viability or the metabolic properties of the bacterium comprising biomineralized ferritins.

The inventors have observed that the mineralized bacteria are still able to divide after biomineralization. Moreover, a fixed number of magnetic bacteria keep their magnetic properties through cell division. The conservation of magnetic properties through division is due to the asymmetrical transmission of iron oxides ferritin-enriched bodies to daughter cells. In contrast, in the case of symmetric divisions (e.g. absence of clusters of iron oxides ferritin-enriched bodies), a strong dilution of the magnetic properties at each cell cycle should occur with a reduction of about 10-fold after 3 generations.

In addition, the inventors observed that biomineralization with a final concentration of $Fe^{2+}$ in step b) around 0.1-0.15 mM (100-150 μM) results in obtaining ferritin-expressing bacteria that were not attracted by magnetic forces, in contrast with ferritin-expressing bacteria biomineralized with 2 mM of $Fe^{2+}$, made in the same conditions. This difference precludes the use of 100 μM mineralized bacteria for biotechnological applications. Without wanting to be bound to a theory, the inventors consider that the amount of iron bound in the nanocage is critical for the magnetic properties to be achieved.

In practice, suitable sources of $Fe^{2+}$ encompass $FeCl_2$ and $FeSO_4$. In some embodiments, the culture medium comprising $Fe^{2+}$ may be a culture medium supplemented with suitable amounts of $Fe^{2+}$. Alternatively, the medium comprising $Fe^{2+}$ may be a Mohr's salt medium or a mixture between $Fe^{2+}/Fe^{3+}$.

In some embodiments, the biomineralization step may be performed for about at least 5 h, in particular for about 6 h to about 24 h. Within the scope of the instant invention, the expression "at least 5 h" encompasses 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 25 h, 26 h, 27 h, 28 h, 29 h, 30 h. Within the scope of the instant invention, the expression "for about 6 h to about 24 h" encompasses about 6 h, 7 h, 8 h, 9 h, 10 h, 11 h, 12 h, 13 h, 14 h, 15 h, 16 h, 17 h, 18 h, 19 h, 20 h, 21 h, 22 h, 23 h and about 24 h.

In certain embodiments, the biomineralization step may be performed on a bacterial culture having an optical density (O.D.) at 600 nm of at least about 0.3, preferably an O.D. comprised from about 0.3 to about 1.0. As used herein, the expression "from about 0.3 to about 1.0" includes 0.3, 0.4, 0.5, 0.6, 0.7, 0.8, 0.9 and 1.0.

The biomineralization of the prokaryotic ferritin may be assessed by any suitable technique known from the state of the art. In some embodiments, biomineralization of the prokaryotic ferritin may be assessed by electron microscopy, in particular high-resolution transmission electron microscopy (HRTEM), Cryo-TEM (cryogenic transmission electron microscopy coupled with EDXS (energy dispersive X-ray spectroscopy)), or energy dispersive X-ray spectroscopy, XAS (X-ray absorption spectroscopy) as XANES (X-ray absorption near edge structure), EXAFS (Extended X-ray absorption fine structure), XMCD (X-ray magnetic circular dichroism), X-ray diffraction techniques, low-temperature magnetic techniques (VSM) and semi-quantitative chemical analysis (ICP analysis, ferrozine assay).

One aspect of the instant invention pertains to a magnetic nanocage comprising biomineralized ferritin from an archaeon, in particular an archaeon from the genus *Pyrococcus*.

One aspect of the instant invention pertains to a magnetic nanocage comprising biomineralized ferritins from *Pyrococcus furiosus*.

In some embodiments, the magnetic nanocage is originating from a recombinant bacterium.

In practice, the bacteria expressing a heterologous ferritin may be contacted with $Fe^{2+}$ in order for the biomineralization to occur and to produce magnetic nanocages. As used herein, a nanocage refers to the structure achieved by the self-assembly of 24 ferritins. As used herein, a magnetic nanocage refers a nanocage wherein iron oxide condensed phases are confined into the ferritins. Subsequently, bacteria may be broken by any suitable technique, e.g. by osmotic shock, sonication or by exerting a pressure (French press), in order to recover the nanocages.

In some embodiments, the magnetic nanocages according to the invention form inclusion bodies within the producing recombinant bacterium. As used herein, the term "inclusion bodies" refers to aggregates of proteins, forming dense electron-refractile particles in the cytoplasm of bacteria.

In certain embodiments, the nanocage comprises at least about 250 iron atoms, in particular, at least about 250 iron atoms bound per 24 ferritins (or 24 ferritin subunits). In some embodiments, the nanocage comprises at least about 500 iron atoms, preferably at least about 750 iron atoms, more preferably at least about 1,000 iron atoms.

Within the scope of the invention, the expression "at least about 250 iron atoms" includes 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500 or more iron atoms.

In some embodiments, the ferritin is fused to a tag to facilitate the purification process.

In some embodiments, the nanocage has an external diameter of from about 12 nm to about 16 nm. Within the scope of the instant invention, the expression "from about 12 nm to about 16 nm" encompasses 12, 13, 14, 15 and 16 nm.

In certain embodiments, the magnetic nanocage is a functionalized nanocage. As used herein, the term "functionalized nanocage" refers to the attribution of a specific function to the nanocage that is not naturally present on the nanocage. Non-limitative examples of such functions are target recognition, target binding, fluorescence, target invasion.

Non-therapeutic uses and methods according to the instant invention may be performed in vivo, ex vivo and in vitro, in particular ex vivo and in vitro.

One aspect of the invention relates to the use of a recombinant bacterium according to the instant invention for its magnetic properties.

In some embodiments, the recombinant, alive and metabolically active bacteria, in particular magnetic bacteria, expressing a heterologous prokaryotic ferritin according to the invention may be concentrated and/or sorted from a complex medium by a magnetic field. As used herein, the term "concentrated" refers to a local increased concentration of the bacteria with respect to the whole medium in which they are spread. The concentration of the bacteria according to the instant invention may be performed at the near vicinity of the magnet applying the magnetic field. As used herein, the term “sorted” refers to the result of the physical separation of the bacteria according to the instant invention from other microorganisms that do not express the heterologous prokaryotic ferritin, in particular bacteria.

As used herein, the expression “complex environment” refers to an environment comprising various organic entities (e.g. proteins, lipids, carbohydrates, polymers) and/or inorganic entities (e.g. trace elements) and/or living entities, in particular microorganisms. In some embodiments, the complex environment may originate from the environment or from a living organism. Non-limited examples of complex environment originating from the environment may encompass sea water, lake water, river water, sewage water, soil, mud. Non-limited examples of complex environment originating from a living organism may encompass whole blood, serum, plasma, cerebrospinal fluid, sputum, pleural fluid, peritoneal fluid, lymphatic fluid, amniotic fluid, saliva, semen, feces and urine.

In some embodiments, the bacterium according to the instant invention may be of use as a biosensor, in particular for the detection and/or the capture of one or more target chemical substance(s) and/or one or more organism(s) in a complex environment.

In some aspect, the invention pertains to a method for the detection of one or more target chemical substance(s) and/or one or more organism(s) comprised in a complex environment, said method comprises the steps of:

a) contacting bacteria according to the instant invention with said complex environment so as to allow the interaction of said one or more target chemical substance(s) and/or one or more microorganism(s) by said bacteria;
b) applying a magnetic field so as to concentrate and/or sort the bacteria;
c) detecting a signal resulting from the interaction of said one or more target chemical substance(s) and/or one or more microorganism(s) by said bacteria, wherein the said detection of a signal is indicative of the presence of said one or more target chemical substance(s) and/or one or more microorganism(s) by said bacteria in said complex environment.

As used herein, the term “biosensor” refers to a bacterium programmed to react with a target substance and to emit a signal.

In some embodiments, the target chemical substance is a substance to be analyzed in a given complex environment. In practice, the bacteria, as biosensors, recognize the substance to be analyzed and produce in turn a signal. At this stage, the signal cannot be quantified because of its dilution in the said environment. Upon application of a magnetic field, the bacteria are concentrated, which concentrates the signal that can now be quantified. The level of the signal allows for a direct quantification of the substance comprised in a given complex environment.

As illustrated in the example below, the bacteria according to the instant invention may be programmed to detect Acyl Homoserine Lactone (AHL) molecules in a given sample. AHL is a compound synthesized and secreted by microorganisms, in particular pathogenic bacteria, and that participates in the quorum sensing. The bacteria according to the invention may be further programmed to emit fluorescence (the signal), upon binding and internalization of the AHL molecules. This may be achieved by fusing the gene encoding a fluorescent protein with a promoter that is sensitive to AHL. Upon application of a magnetic field, the bacteria according to the instant invention are concentrated, which allows the fluorescence to be quantified. The quantification of the fluorescence is a direct readout of the amount of AHL in the sample.

In some embodiments, the target chemical substance is a pollutant, in particular selected in a group comprising chlorine, hydrocarbons (e.g. from oil), endocrine disrupters, heavy metals, residues originating from the pharmaceutical industry, residues originating from intensive farming (e.g. pesticide residues, fertilizers), radioelements.

In practice, the recombinant magnetic bacterium according to the invention, as a biosensor, may be of use for detecting heavy metals such as arsenic, cadmium, chromium, copper, mercury, nickel, lead, selenium, zinc. Advantageously, the detection may be coupled with a quantification system, by the mean of an emitted signal, such as e.g. a change in optical density, the emission of fluorescence, an increase in an enzymatic activity.

In some embodiments, the bacterium according to the instant invention, as a biosensor, may be further used for the bioremediation of polluted soils, waters or any other environment. In practice, the detection of the pollutant may also be coupled to a sequestration system allowing the bacterium to capture the pollutant.

In practice, the bacteria according to the invention are put into contact with the polluted environment for a duration allowing the pollutant to be detected and captured by the bacteria. A magnetic field is then applied in order to attract the magnetic bacteria and remove them from the environment.

Therefore, another aspect of the invention pertains to a method for the removal of a pollutant from a polluted environment, said method comprising the steps of:

a) contacting bacteria according to the instant invention with said polluted environment so as to allow the capture of said pollutant by said bacteria;
b) applying a magnetic field to concentrate and/or sort the bacteria;
c) removing said bacteria having captured the said pollutant from said environment.

In some embodiments, the target chemical substance may be selected in a group comprising a hormone, a cytokine, a vitamin. Said target chemical substance may be originating from a sample collected from a living organism, in particular from a mammal animal, in particular from a human, for non-therapeutic detection purposes.

In some embodiment, the organism is a microorganism, in particular an alga, an archaeon, a bacterium, a fungus, a phage, a virus, a yeast.

In practice, said sample to be analyzed may be a body fluid selected in a group comprising whole blood, serum, plasma, cerebrospinal fluid, sputum, pleural fluid, peritoneal fluid, lymphatic fluid, amniotic fluid, saliva, semen, feces and urine.

Therefore, one aspect of the invention relates to a method for detecting a non-pathological state in an individual, said method comprising:

a) contacting bacteria according to the instant invention with a sample collected from an individual as to allow the interaction of said target chemical substance possibly comprised in said sample by said bacteria;
b) applying a magnetic field to concentrate and/or sort the bacteria;
c) detecting a signal resulting from the interaction of said target chemical substance by said bacteria, wherein the said detection of a signal is indicative of a non-pathological state in said individual.

Illustratively, the target chemical substance may be the hormone hCG, which may be detected by a programmed bacterium according to the instant invention in a urine sample from a female individual, as to detect a pregnancy in said female individual.

In some embodiments, the bacterium according to the instant invention may be of use for the surface display of a ligand, preferably an antibody, a nanobody, and/or an antigen.

Within the scope of the invention, the term "ligand" refers to a molecule capable of forming a complex with another molecule.

In practice, when the surface display involves an antigen, this system may allow the screening of corresponding antibodies or nanobodies having an affinity for said antigen.

Inversely, when the surface display involves antibodies or nanobodies, this system may allow the screening of corresponding antigens.

The application of a magnetic field would concentrate the magnetic bacteria according to the invention, and further analysis of bound antigen to the antibody or of bound antibody to the antigen may be performed according to the methods available in the state of the art. In practice, complexes antigen-antibody may be analyzed by chromatography, in particular high-performance liquid chromatography (HPLC) and/or mass spectrometry.

As illustrated in the examples section below, the inventors have shown that an antigen at the surface of mCherry-expressing magnetic bacteria according to the invention may bind to the corresponding nanobody at the surface of a non-magnetic GFP-expressing bacteria. Upon application of a magnetic field, both the red fluorescence from mCherry and the green fluorescence from GFP are colocalizing at the vicinity of the magnet. This demonstrates antigen-expressing magnetic bacteria can capture targeted bacteria and them allow the transport and accumulation of the target cells upon magnetic field application.

This system may be generalized for the screening of two interacting domains.

In some embodiments, the bacterium according to the instant invention may be of use for the production of functionalized magnetic nanocages comprising biomineralized ferritins from *Pyrococcus furiosus*.

Therapeutic uses and methods according to the instant invention may be performed in vivo, ex vivo and in vitro, in particular ex vivo and in vitro.

In one aspect, the invention relates to a recombinant bacterium according to the instant invention for use as a medicament.

Another aspect of the invention pertains to a recombinant bacterium according to the instant invention for use in therapy.

The instant invention also pertains to the use of a recombinant bacterium according to the instant invention for the preparation of a medicament. Another aspect of the instant invention further relates to the use of a recombinant bacterium according to the instant invention for the manufacture of a medicament.

In some embodiments, the invention relates to a method to treat and/or prevent a disease comprising the administration of a therapeutic efficient amount of a recombinant bacterium according to the instant invention.

In some embodiments, the recombinant bacterium according to the instant invention is for use as a molecule delivery system.

In some embodiments, the molecule is a therapeutic molecule. Non-limitative examples of therapeutic molecule may encompass antihistaminic compounds, antalgic compounds, anti-inflammatory compounds, anti-anemic compounds, anti-acneic compounds, antifungal compounds, antiherpetic compounds, antiparasitic compounds, anti-acidic compounds, antitumor compounds, and the like.

In some embodiments, the recombinant bacterium according to the invention may comprise a surface ligand that specifically binds to the surface of a target cell.

In some embodiments, the recombinant bacterium according to the instant invention is for use for the therapeutic diagnostic of a disorder.

In certain embodiments, the magnetic bacterium according to the invention is for use as a contrast agent. As illustrated in the example section below, the inventors have shown that the bacterium according to the invention may behave as a contrast agent and therefore be useful for diagnosis purposes, in particular by NMR or MRI techniques.

As for the biosensor properties disclosed above, the recombinant bacterium according to the instant invention may be programmed to detect a biomarker specific to a disorder, and emit a signal upon said detection.

Within the scope of the instant invention, a disorder may be a genetic disorder, an autoimmune disorder, an infectious disorder, an inflammation disorder or a cancer.

Another aspect of the invention relates to a method for diagnosing a disorder, said method comprising the steps of:

a) contacting bacteria according to the instant invention with a sample collected from an individual as to allow the interaction of a biomarker specific to said disorder by said bacteria;
b) applying a magnetic field to concentrate and/or sort the bacteria;
c) detecting a signal resulting from the interaction of said biomarker by said bacteria, wherein the said detection of a signal is indicative of the occurrence in a disorder in said individual.

In some embodiments, the autoimmune disorder is selected in the non-limitative group comprising type 1 diabetes, rheumatoid arthritis, psoriasis, systemic lupus erythematosus, inflammatory bowel disease, celiac disease.

In certain embodiments, the infectious disorder is selected in the non-limitative group comprising Anaplasmosis; Anthrax; Babesiosis; Botulism; Brucellosis; *Burkholderia mallei* infection (glanders); *Burkholderia pseudomallei* infection (melioidosis); *Burkgolderia cepacia*; Campylobacteriosis; Carbapenem-resistant Enterobacteriaceae infection (CRE); Chancroid; Chikungunya infection; *Chlamydia* infection; Ciguatera; *Clostridium dificile* infection; *Clostridium perfringens* infection (Epsilon Toxin); Coccidioidomycosis fungal infection (Valley fever); Creutzfeldt-Jacob Disease, transmissible spongiform (CJD); Cryptosporidiosis; Cyclosporiasis; Dengue Fever, Diphtheria; *E. coli* infection; Eastern Equine Encephalitis (EEE); Ebola Haemorrhagic Fever (Ebola); Ehrlichiosis; Arboviral or parainfectious encephalitis; Non-polio enterovirus infection; D68 enterovirus infection, (EV-D68); Giardiasis; Gonococcal infection (Gonorrhoea); Granuloma inguinale; Type B *Haemophilus influenza* disease, (Hib or H-flu); Hantavirus pulmonary syndrome (HPS); Haemolytic uremic syndrome (HUS); Hepatitis A (Hep A); Hepatitis B (Hep B); Hepatitis C (Hep C); Hepatitis D (Hep D); Hepatitis E (Hep E); Herpes; Herpes zoster, zoster VZV (Shingles); Histoplasmosis; Human Immunodeficiency Virus/AIDS (HIV/AIDS); Human Papillomavirus (HPV); Influenza (Flu); Lead poisoning; Legionellosis (Legionnaires Disease); Leprosy (Hansens Disease); Leptospirosis; Listeriosis; Lyme Disease; Lymphogranuloma venereum infection (LVG); Malaria; Measles; Viral meningitis; Meningococcal disease; Middle East respiratory syndrome coronavirus (MERS-CoV); Mumps; Norovirus; Paralytic shellfish poisoning; Pediculosis (lice, head and body lice); Pelvic inflammatory disease (PID); Pertussis; Bubonic, septicemic or pneumonic plague; Pneumococcal disease; Poliomyelitis (Polio); *Pseudomonas aeruginosa* infection; Psittacosis; Pthiriasis (crabs; pubic lice infestation); Pustular rash diseases (small pox, monkeypox, cowpox); Q-Fever, Rabies; Ricin poisoning; Rickettsiosis (Rocky Mountain Spotted Fever); Rubella, including congenital rubella (German Measles); Salmonellosis gastroenteritis infection; Scabies infestation; Scombroid; Severe acute respiratory syndrome (SARS); Shigellosis gastroenteritis infection; Smallpox; Methicillin-resistant Staphylococcal infection (MRSA); Staphylococcal food poisoning; Vancomycin intermediate Staphylococcal infection (VISA); Vancomycin resistant Staphylococcal infection (VRSA); Streptococcal disease, Group A; Streptococcal disease, Group B; Streptococcal toxic-shock syndrome (STSS); Primary, secondary, early latent, late latent or congenital syphilis; Tetanus infection (Lock Jaw); Trichinosis; Tuberculosis (TB); Latent tuberculosis (LTBI); Tularaemia (rabbit fever); Typhoid fever, Group D; Typhus; Vaginosis; Varicella (chickenpox); *Vibrio cholerae* infection (Cholera); Vibriosis (*Vibrio*); Viral haemorrhagic fever (Ebola, Lassa, Marburg); West Nile virus infection; Yellow Fever, *Yersinia* infection and Zika virus infection.

In some embodiments, the cancer is selected in the non-limitative group comprising a bladder cancer, a bone cancer, a brain cancer, a breast cancer, a cancer of the central nervous system, a cancer of the cervix, a cancer of the upper aero digestive tract, a colorectal cancer, an endometrial cancer, a germ cell cancer, a glioblastoma, a Hodgkin lymphoma, a kidney cancer, a laryngeal cancer, a leukemia, a liver cancer, a lung cancer, a myeloma, a nephroblastoma (Wilms tumor), a neuroblastoma, a non-Hodgkin lymphoma, an esophageal cancer, an osteosarcoma, an ovarian cancer, a pancreatic cancer, a pleural cancer, a prostate cancer, a retinoblastoma, a skin cancer (including a melanoma), a small intestine cancer, a soft tissue sarcoma, a stomach cancer, a testicular cancer and a thyroid cancer.

In some embodiments, the biomarker may be selected in the non-limitative group comprising a toxin, an antigen, a hormone, a metabolite, a vitamin, an antibody, a cytokine, a blood cell, a cancerous cell, a phage, a pathogenic microorganism.

In some embodiments, the pathogenic microorganism is a virus, in particular selected in a group comprising an adenovirus, an adeno-associated virus, an alphavirus, a herpesvirus, a lentivirus, a non-integrative lentivirus, a retrovirus and a vaccinia virus.

In certain embodiments, the recombinant bacterium according to the instant invention may be contacted with a sample to be analyzed originating from a living organism, in particular from a mammal animal, in particular from a human, for diagnostic purposes.

In practice, the sample to be analyzed may be a body fluid selected in a group comprising whole blood, serum, plasma, cerebrospinal fluid, sputum, pleural fluid, peritoneal fluid, lymphatic fluid, amniotic fluid, semen, saliva, feces and urine.

In certain embodiments, a positive detection may be coupled to the emission of a signal, which may be detected and/or measured upon application of a magnetic field to concentrate the bacteria.

In some embodiments, the recombinant bacterium according to the instant invention may capture and trap a virus, a pathogenic microorganism and/or a cancer cell.

In certain embodiments, non-limitative examples of a target cell according to the instant invention may encompass a cell of the central nervous system, an epithelial cell, a muscular cell, an embryonic cell, a germ cell, a stem cell, a progenitor cell, a hematopoietic stem cell, a hematopoietic progenitor cell, an induced Pluripotent Stem Cell (iPSC).

In some particular embodiments, the target cell is not a stem cell, a progenitor cell, a germinal cell or an embryonic cell.

In some embodiments, the target cell may originate from a tissue selected in a group comprising a muscle tissue, a nervous tissue, a connective tissue, and an epithelial tissue.

In some embodiments, the target cell may originate from an organ selected in a group comprising a bladder, a bone, a brain, a breast, a central nervous system, a cervix, a colon, an endometrium, a kidney, a larynx, a liver, a lung, an esophagus, an ovarian, a pancreas, a pleura, a prostate, a rectum, a retina, a salivary gland, a skin, a small intestine, a soft tissue, a stomach, a testis, a thyroid, an uterus, a vagina.

As illustrated in the example hereunder, the bacteria according the instant invention may be programmed to capture and trap a specific cell. The inventors have shown that the magnetic bacteria according to the invention may capture other non-magnetic bacteria, taking advantage of the common principle of antigen/antibody interactions.

In some embodiments, the recombinant bacterium according to the instant invention is for use for the surface display of a protein of interest that recognizes and/or penetrates a target cell.

In certain embodiments, the target cell is a mammal target cell, preferably a human target cell.

In some embodiments, the target cell is a cell in need of treatment, in particular a diseased cell, more preferably a cancer cell. In certain embodiments, the cancer cell is selected in a group comprising a leukaemia cell, a carcinoma cell, a sarcoma cell, a lymphoma cell, a craniopharyngioma cell, a bastoma cell, a melanoma cell, a glioma cell and a mesothelioma cell.

As illustrated in the examples below, the magnetic bacterium according to the instant invention may express invasin from *Yersinia pseudotuberculosis*, which enables the bacteria to invade a target cancer cell. The bacterium may further encode a system to synthesize and release a cytotoxic agent which may promote the killing of the target cell.

For both the non-therapeutic and the therapeutic uses and methods according to the instant invention, the total number or the relative number of bacteria according to the instant invention may be adapted accordingly.

In some embodiments, the total number of bacteria according to the invention may represent $10^4$ to $10^{15}$ CFU. Within the scope of the instant invention, the expression "$10^4$ to $10^{15}$ CFU" encompasses $10^4$, $10^5$, $10^6$, $10^7$, $10^8$, $10^9$, $10^{10}$, $10^{11}$, $10^{12}$, $10^{13}$, $10^{14}$ and $10^{15}$ CFU. In some embodiments, the relative number of bacteria according to the invention may represent $10^4$ to $10^{15}$ CFU/ml. Within the scope of the instant invention, the expression "$10^4$ to $10^{15}$ CFU/ml" encompasses $10^4$, $10^5$, $10^6$, $10^7$, $10^8$, $10^9$, $10^{10}$, $10^{11}$, $10^{12}$, $10^{13}$, $10^{14}$ and $10^{15}$ CFU/ml. In some embodiments, the relative number of bacteria according to the invention may represent $10^4$ to $10^{15}$ CFU/$cm^3$. Within the scope of the instant invention, the expression "$10^4$ to $10^{15}$ CFU/$cm^3$" encompasses $10^4$, $10^5$, $10^6$, $10^7$, $10^8$, $10^9$, $10^{10}$, $10^{11}$, $10^{12}$, $10^{13}$, $10^{14}$ and $10^{15}$ CFU/$cm^3$. In some embodiments, the relative number of bacteria according to the invention may represent $10^4$ to $10^{15}$ CFU/mg. Within the scope of the instant invention, the expression "$10^4$ to $10^{15}$ CFU/mg" encompasses $10^4$, $10^5$, $10^6$, $10^7$, $10^8$, $10^9$, $10^{10}$, $10^{11}$, $10^{12}$, $10^{13}$, $10^{14}$ and $101^5$ CFU/mg.

EXAMPLES

The present invention is further illustrated by the following examples.

Example 1: Obtention of MagEcoli and Uses Thereof

1—Materials and Methods
1.1—Chemicals

Kanamycin, Chloramphenicol, Ampicillin, Spectinomycin, Mohr's Salt, LB browth, M9 Browth, Glycerol, Agar, Sucrose, IPTG, Mineral oil, DMSO, Iron citrate (III), PBS, EDTA, Imidazole, Lysozyme, Triton X100, AEBSF, Protease inhibitor cocktail were purchased from SIGMA-ALDRICH®.

Anhydro tetracyclin was a gift from Olivier Espeli; Arlacel P135 was purchased from CRODA®; AHL was purchased from BERTIN BIOREAGENT®; Optiprep was purchased from StemCell®; BSA was purchased from BIO-RAD®.

1.2—Molecular Vectors and Strains

The *Pyrococcus Furiosus* ferritins were fused at their N-terminal to mCherry or Emerald GFP (EmGFP) and were cloned into pet28, pGBM3/4/5/6, and pet28duet plasmids.

Quorum sensing genes (pLux01 and pTD103luxIsfGFP) and specific adhesion genes (pDSG375 and pDSG419) were purchased from ADDGENE®.

TABLE 1

Plasmids used herein

| Plasmid | Gene expression | Resistance |
|---|---|---|
| pet28_mCherrry-Ferritin | *Pyrococcus Furiosus* ferritin fused with mCherry | Kanamycin |
| pet28_EmGFP-Ferritin | *Pyrococcus Furiosus* ferritin fused with EmGFP | Kanamycin |
| pGBM3_mCherry-Ferritin<br>pGBM4_mCherry-Ferritin<br>pGBM5_mCherry-Ferritin<br>pGBM6_mCherry-Ferritin | *Pyrococcus Furiosus* ferritin fused with mCherry | Spectinomycin/Streptomycin |
| pGBM3_EmGFP-Ferritin<br>pGBM4_EmGFP-Ferritin<br>pGBM5_EmGFP-Ferritin<br>pGBM6_EmGFP-Ferritin | *Pyrococcus Furiosus* ferritin fused with EmGFP | Spectinomycin/Streptomycin |
| pET28duet-FKBP.mCherry.Ferritin_FRB.EmGFP.Ferritin | Histidine-6X, FKBP-mCherry-Ferritin and FRB-EmGFP-Ferritin | Kanamycin |
| pET28duet-FRB.EmGFP.Ferritin_FKBP.mCherry.Ferritin | 6 Histidines, FRB- EmGFP -Ferritin and FKBP-mCherry-Ferritin | Kanamycin |
| pTD103luxIsfGFP[a] | AHL and sfGFP | Kanamycin |
| pLux01[b] | mRFP1 upon AHL detection | Chloramphenicol |
| pDSG375[c] | Nanobody | Kanamycin |
| pDSG419[c] | Antigen | Kanamycin |

[a]Prindle, A., Samayoa, P., Razinkov, I., Danino, T., Tsimring, L. S., & Hasty, J. A sensing array of radically coupled genetic 'biopixels'. *Nature* 481(7379), 39 (2012).
[b]Florea, Michael, et al. Engineering control of bacterial cellulose production using a genetic toolkit and a new cellulose-producing strain. *Proceedings of the National Academy of Sciences* 113.24: E3431-E3440 (2016).
[c]Glass, D. S., & Riedel-Kruse, I. H. A synthetic bacterial cell-cell adhesion toolbox for programming multicellular morphologies and patterns. Cell, 174(3), 649-658, (2018).

Rosetta strains were used for the experiments of biomineralization, magnetophoresis, and cell divisions. The plasmids inserted were pet28_mCherry-Ftn, and pet28_GFP-Ftn when mentioned.

TABLE 2 bacterial strains used herein

| Experimental strain | Assay |
|---|---|
| *E. Coli*: Rosetta ™ (DE3) pLysS | Biomineralization, magnetophoresis, cell divisions, extraction of in vivo mineralized ferritins |
| *E. Coli*: SIGMA-ALDRICH ® BL21 | Magnetic biosensor, cell invasion |
| *E. Coli*: MG1655[a] | Magnetic biosensor, magnetic AHL-producer, antigen/nanobody recognition, cell invasion |
| *E. Coli*: THERMO-FISHER ® dH10β[b] | Cloning |
| HeLa cell/Lovo cells | Cell invasion |

[a]Gift from Olivier Espeli.
[b]from NOVAGEN ®.

1.3—Transformation

All plasmids were incorporated into electrocompetent bacteria via electroporation as described in Maniatis et al. (Molecular cloning: a laboratory manual. Cold Spring Harbor Laboratory, 1982).

1.4—Biomineralization Protocol

Bacteria were grown overnight in LB medium. The next day, they were diluted and grown into fresh LB medium with antibiotics at 37° C. under agitation for approximatively 2 hours, until they reach an optical density of 0.6.

500 µM of IPTG was added into the medium for the pet28 derived plasmids and bacteria were let at 37° C. under agitation for 30 min. Simultaneously a fresh solution of Mohr's salt was made (100 mM of $Fe^{2+}$ solution) and then added to the bacteria to a final concentration of 1 to 4 mM. Bacteria were grown overnight at 37° C. (about 16 hours+/−10%). The next morning, they were washed after centrifugation to remove iron oxide residues from the LB and placed into the desired buffer (for observation or further experiments).

1.5—Ultrathin Section Transmission Electron Microscopy

*E. coli* cells were fixed for 2 hours in 2% glutaraldehyde in 0.1 M Sorensen phosphate buffer and washed with iso osmolar phosphate buffer. After the samples were fixed for 1 hour with 1% of osmium tetroxide and washed with iso osmolar phosphate buffer. After repeated washing, the samples were dehydrated through an ethanol series and embedded in epoxy resin (ERL 4206) in beem capsules, which polymerized at 55° C. for 48 hours. Ultrathin sections were obtained using a diatome diamond knife in a Leica UCT ultramicrotome and deposited onto a 300-mesh carbon-coated grid. TEM images were obtained on a Jeol 2100 F microscope. This machine, operating at 200 kV, is equipped with a field emission gun, an ultra-high-resolution pole piece, and an ultrathin window JEOL detector.

1.6—Magnetophoresis Set Up

For the magnetophoresis experiments, freshly mineralized bacteria were washed twice in M9 medium and diluted to an optical density of approximatively 0.6 (when not mentioned) in M9 supplemented with sucrose (to prevent sedimentation). M9 was replaced with LB and sucrose with Optiprep 20% in the assays of AHL detection by magnetic bacteria, and AHL release by MagEcoli.

A water-in-oil emulsion was formed by mixing up 99 µL of mineral oil supplemented with a block copolymer at 0.4 g/L (ArlacelP135) and 1 µL of bacteria. The emulsion was inserted into a round capillary (1 mm of diameter) fixed on a microscopic slide (32×40 mm). The capillary was sealed with vitrex and a small magnet was placed at one side (cubic magnet FeNd 3 mm, Supermagnet), the N-S axis being perpendicular to the capillary's direction.

Observations were made using epifluorescence microscopy.

1.7—Study of the Transmission of Magnetism as a Function of Cell Division with Magnetophoresis Biomineralized bacteria (4 mM of $Fe^{2+}$) were diluted to an optical density of around 0.1 into fresh LB medium. Depending on the context, 500 μM of IPTG and kanamycin were added to induce the constant production of mCherry-Ferritin during growth until the bacteria reached the desired optical density. For magnetophoresis, bacteria were concentrated and washed twice into M9 medium.

1.8—Single-Cell Observation of Dividing Bacteria

To perform visualization of bacteria during cell division, mineralized bacteria (2 mM of $Fe^{2+}$) were washed in LB medium and then diluted into a fresh LB medium (kanamycin) to an Optical Density at 600 nm of 0.1. Bacteria were put at 37° C. under agitation and Optical Density at 600 nm monitored growth. For single-cell observation, bacteria were washed and concentrated into M9 medium. They were spread on an agarose pad (LB, 2%) and observed on epifluorescence microscopy.

1.9—Detection of Small Molecules (AHL) Via Magnetic Bacteria

Overnight cultures of SIGMA-ALDRICH® BL21 bacteria co-transformed with pet28_GFP-Ferritin and pLux01 plasmids were made with the corresponding antibiotics. The next days, bacteria were biomineralized with 4 mM of $Fe^{2+}$ and MG1655 bacteria transformed with the plasmid pTD1003luxIsfGFP were overnight cultured with the corresponding antibiotic. In the morning, mineralized bacteria and precultures were washed twice in LB medium and observed by magnetophoresis.

Further assays were performed with 10 μM of commercially available AHL diluted in DMSO or the supernatant of the first centrifugation of preculture (bio-produced AHL) added to the washed magnetic sensors. Controls were made without AHL and without $Fe^{2+}$ (not mineralized sensors).

1.10—Production of AHL Via Magnetic Bacteria

MG1655 bacteria co-transformed with the plasmid pTD1003luxIsfGFP and a pGBM4_GFP-Ferritin plasmid were mineralized with 4 mM of $Fe^{2+}$ while MG1655 transformed with the plasmid pLux01 were diluted in LB and antibiotic for overnight precultures. In the morning, precultures of sensors were diluted 1/100 in fresh LB with antibiotics and let grow at 37° C. for 2 hours (until they reach the exponential phase). Then mineralized AHL-producing bacteria and sensor bacteria were washed twice in LB medium and observed by magnetophoresis.

Controls were made without AHL-producing bacteria to check for the absence of mRFP1 fluorescence without AHL, and without iron II (not mineralized AHL-producers).

1.11—Spatial Constraints of Cell Communication on Solid Surface Mediated by Pre-Sorted ΔHL-Producer Magnetic Bacteria The same bacteria used for the production of AHL via magnetic bacteria were employed. 4 mM mineralized AHL-producing bacteria were washed twice in LB medium and diluted to the desired concentration. Waterproof magnets (teflon coated Nd/Fe magnet, 5×5 mm, supermagnet) were incubated for 2 hours in 1 mL of magnetic bacteria solution in 1.5 mL or 2 mL eppendorf, under agitation. In the meantime, overnight precultures of sensors were diluted in fresh LB and antibiotic to 1/100 for 2 hours to reach the exponential phase. Next, sensors bacteria were spread on a free antibiotics petri dish and the magnet was deposited at its center. The set-up was left for 24 hours at 37° C. Then, the magnet was removed and pictures were taken using a Chemidoc MP imaging system (Biorad, in colorimetric, Alexa488 and Alexa546 channels).

The control with not mineralized AHL-producers was performed for each assay at the same time.

1.12—Capture and Spatial Attraction of Targeted Bacteria by Antigen/Antibody Recognition MG1655 bacteria were co-transformed with pDSG419 and pGBM4-mCherry-Ferritin plasmids, and other MG1655 were co-transformed with pDSG375 and pGBM4-GFP-Ferritin plasmids. The first strain of bacteria was mineralized with 4 mM or $Fe^{2+}$ in the presence of 100 ng/mL of anhydro tetracycline and antibiotics. The second strain was diluted in LB also with 100 ng/mL of anhydro tetracycline and antibiotics for overnight preculture. The next day, both populations of bacteria were washed twice with M9 medium. The two strains were mixed in M9 (for aggregates visualization) or M9+sucrose medium at the desired density (for immediate test of magnetophoresis).

After several hours, the mixes in M9 let at room temperature were observed in glass chip chambers to monitor aggregation. On the same day controls without anhydro tetracycline (so without aggregates) and without iron were performed.

1.13—Spatial Modulation of Cell Invasion by MagEcoli

SIGMA-ALDRICH® BL21 co-transformed with the invasin plasmid and the pet28_GFP-Ferritin plasmid (or pet28_mCherry-Ferritin for the control) were biomineralized with 4 mM of $Fe^{2+}$.

Bacteria were washed with PBS just after biomineralization, and were diluted in PBS+20% Optiprep (to prevent sedimentation) to an optical density of 0.02.

On each ibidi slide containing confluent HeLa cells, 2 mL of bacteria in PBS were added. Each ibidi was placed above a magnet (FeNd square 10 mm, supermagnet, FeNd parallelepiped 15 mm×4 mm×4 mm for the test on MG1655) in an incubator providing a constant temperature of 37° C. and carbon dioxide supply, for 4 hours.

After incubation, the PBS was removed and the ibidi were filled with 2 mL of DMEM+gentamicin (40 μg/mL). Immediately, it was replaced by 2 ml of DMEM+gentamicin (40 μg/mL)+FBS 10%. The system was let 1 hour at 37° C. to kill all the bacteria that had not been able to enter into cells.

Then, after washing with PBS, cells were fixed with paraformaldehyde (PFA) 4% for 5 min+20 min. After washing with PBS, cells were permeabilized with PBS and Triton 0.5% and stained with DAPI and Actistain 647 for 1 hour.

Other strain was tested: MG1655 co-transformed with the invasin plasmid and pGBM4_GFP-Ferritin plasmid (or pGBM4_mCherry-Ferritin for the diamagnetic control) on Lovo cells.

1.14—Extraction of Mineralized Ferritins from Biomineralized Bacteria

Rosetta bacteria were transformed with the plasmid pET28duet-FKBP.mCherry.Ferritin_FRB.GFP.Ferritin or the plasmid pET28duet-FRB.GFP.Ferritin_FKBP.mCherry-.Ferritin. Overnight culture of bacteria was diluted in LB medium+antibiotics and grow at 37° C. under agitation. After reaching an optical density at 600 nm of 0.6, 500 μM of IPTG, 1 mM of $Fe^{2+}$ (fresh solution Mohr's salt) and 1 mM of $Fe^{3+}$ (freshly made solution of iron acetate) were added. The bacteria were let 16 hours at 16° C. under agitation for biomineralization. Next, biomineralized bacteria were centrifugated at 4500 rpm for 30 minutes at 4° C. Then the bacterial pellet was washed (PBS buffer) and re-suspended with washing buffer (PBS 1×, imidazole 10 mM). Lyzozyme, Triton X100 (0.1%), AEBSF (1 nM) and protease inhibitor were added to lyse the bacteria for 30 minutes on ice. 30 cycles of sonication were applied to the samples and a mechanical lysis was performed. After a 10 minutes centrifugation at 10,000 rpm at 4° C., the supernatant was incubated 2 hours at 4° C. with Ni-Nta beads previously washed and transferred into the washing buffer. The proteins+beads were placed in a column, washed with the same buffer and eluted with the elution buffer (PBS 1×, EDTA 100 mM, imidazole 250 mM, glycerol 5%). Ferritins were dialyzed to replace the buffer with PBS 1×(1 hour+overnight dialysis). On the next day, Nanodrop measurements, SDS page gel and Bradford assay determined the concentration of proteins in the fractions. The fractions with the higher concentrations were used for magnetophoresis.

To induce the formation of clusters of ferritins, mCherry-Ferritins and GFP-Ferritins fractions were mixed in the presence of rapamycin (100 μM final) to induce the heterodimerization of FRB and FKBP and with BSA (to prevent adsorption on the droplet interface) in PBS (Ducasse et al, 2017, *Scie. Report*). A 1% PBS-in-oil emulsion was formed and magnetophoresis was performed using a magnetized tip (radius of curvature of about 25 μm). The tip was then adapted on the N-S axis of a NdFeB permanent magnet (3 mm length) and placed next to oil droplets using a manual micromanipulator (Narishige). With this system the gradient of magnetic field can reach $10^4$ T·m$^{-1}$ at the vicinity of the tip.

1.15—Microscopy Observations

Magnetophoresis experiments were observed using IX81 (OLYMPUS™) epifluorescence microscope equipped with an EM-CCD camera (electron multiplying CCD,C9100-13 or C9100-02,HAMAMATSU™, Corporation), a LED for illumination (Spectra X™, Lumencor), and with ×10 and ×20 objectives. Microscopes were controlled by MicroManager or SimplePCI software.

Confocal imaging was performed using ZEISS™ LSM 710 Meta laser scanning confocal and a ×20 or ×60 objectives. The microscope was controlled with LSM Software Zen 2009.

1.16—Data Analysis

Image analysis were made using Fiji. Running Z projector plug-in was used to observe superimposed trajectories in the magnetophoresis assays.

For the tracking of trajectories, 60 trajectories were tracked for each biomineralization condition. We then transferred (x,y) positions of bacteria tracked on Excel and Matlab for analysis and graphs. Experiments were performed twice for each concentration of iron (at different days).

To count the number of bacteria under agar-gel, Cell-counter was used on composite images (merged of bright field and mCherry). The assay of bacterial growth was duplicated on a different day. For each division of each assay, we counted around 1,000 bacteria. The 1,000 bacteria counted came from different field on the slide. Data were exported to Excel and Matlab for graph.

To count the nucleus and bacteria for the assay of bacterial invasion in cells, we applied the functions Particle Analysis on binary-transformed images (after applying a manual threshold). We counted on 4 different areas crossing the ibidi on the same representative sample. Data were exported to Excel and Matlab for graph.

To quantify magnetic loss during cell division on magnetophoresis movies, we measured the mean intensity with Fiji of a surface of bacteria near the droplets at 89 min and the surface and mean intensity of the droplet at time 0 min. Using excel we divide the intensity of accumulated bacteria by the intensity of all bacteria at t=0, normalized by the respective area:

$$\frac{I \times S}{Idroplet \times Sdroplet}$$

This parameter indicated how many bacteria were attracted as regard as the total amount of bacteria in the droplet. We measured on three different conditions of different days (3 movies). The graphs were made using Matlab.

For the student tests, we used the functions ttest2 on Matlab.

2—Result 2.1—Genetic and Chemical Modifications to Obtain Magnetic Bacteria

Figure 1B:
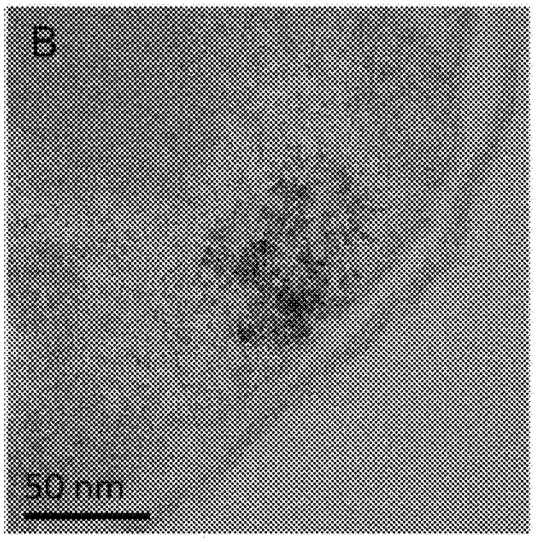
Figure 2:
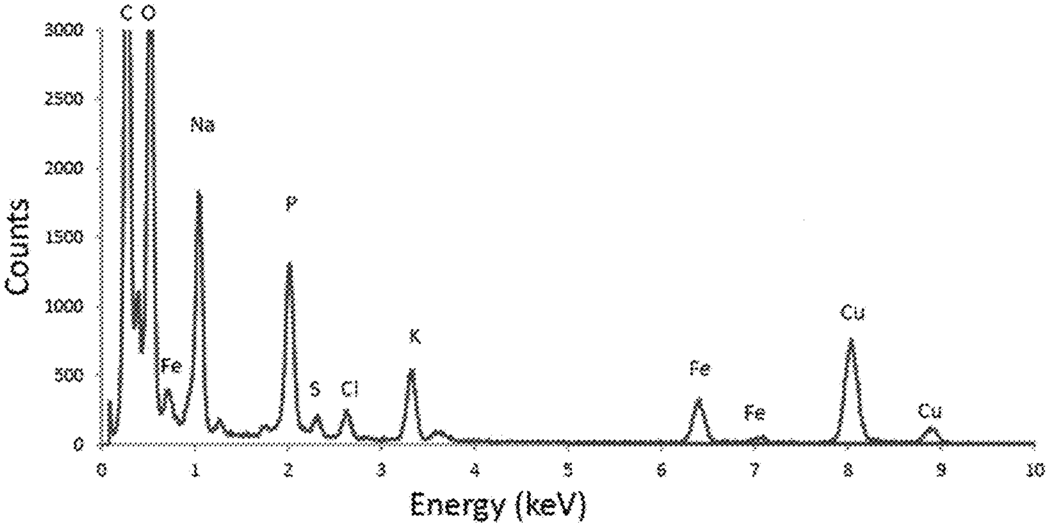
FIG. 2 is a plot showing the energy dispersive X-ray spectroscopy spectra for the electron-dense deposit.

Our strategy to produce iron oxide inclusions in bacteria relied on a two-step process consisting first in overexpressing fluorescently-labelled ferritins and then supplying $Fe^{2+}$ to the growth medium to biomineralize the bacteria. We chose the heterologous production of the iron-storage ferritins derived from *Pyrococcus furiosus* (Tatur et al. A highly thermostable ferritin from the hyperthermophilic archaeal anaerobe *Pyrococcus furiosus. Extremophiles*. April, 10(2): 139-48 (2006); Tatur and Hagen. The dinuclear iron-oxo ferroxidase center of *Pyrococcus furiosus* ferritin is a stable prosthetic group with unexpectedly high reduction potentials. *FEBS Lett. August* 29; 579(21):4729-32 (2005)). After 16 hours of biomineralization, bacteria were washed and then characterized at the nanometer scale using high resolution transmission electron microscopy (HRTEM) images of cross sectioned mineralized *E. coli*. To confirm the presence of nanoparticles in bacteria, we performed high-resolution transmission microscopy (HRTEM) to characterize the morphology, the shape, and the crystal phase of the intracellular cluster. HRTEM images of 60 nm cross-section *Escherichia coli* which overexpressed ferritin mineralized with 2 mM $Fe^{2+}$ showed accumulation of a large electron-dense-deposit at the extremity of the bacteria (FIG. 1A). The intracellular clusters are formed by the aggregation of small nanoparticles (~3-5 nm, FIG. 1B) which is consistent with the cavity size of ferritin nanocages (6 nm). The iron oxide cluster is localized in the cytosol of the bacteria and showed a hyper-accumulation of iron. The electron diffraction pattern of the iron oxide cluster showed that the nanoparticles are completely amorphous. To reveal the elemental composition of the electron-dense deposits, this specific area was analyzed by energy dispersive X-ray spectroscopy. Iron, phosphorous and oxygen were detected within cells (FIG. 2). Scanning transmission electron microscopy (STEM) images of 60 nm thick cross-sections of *Escherichia. coli* overexpressing ferritin cells also showed high atomic density regions in cytosol, quasi-spherical in shape and 100-300 nm in diameter within the cells. Elemental maps and pixel by pixel energy dispersive spectra were obtained. Iron showed unambiguous localization into clusters revealed as area dense to electrons. Phosphorus also accumulated in these clusters and oxygen showed a similar pattern as phosphorus with less contrast.

Altogether those data highlight that biomineralized *E. coli* contain iron oxides ferritin-enriched bodies conferring magnetic properties.

2.2—Spatial Manipulation and Localization of Bacteria Upon Magnetic Forces

To assess the possibility to spatially manipulate biomineralized bacteria, we performed magnetophoretic experiments, which consist in observing the motion of non-motile bacteria submitted to magnetic forces. A mixture of biomineralized bacteria expressing mCherry-ferritin (3 mM iron) and non-mineralized one (expressing EmGFP-ferritin) were diluted in a minimal medium with a density adjusted to prevent bacteria sedimentation (see the 'Materials and Methods' section). The mixture was then confined into water-in-oil droplets to minimize hydrodynamic flow perturbations and facilitate observation. Once formed, the bacteria droplets were dispersed into a capillary next to a permanent magnet generating a gradient of about 10 T/m (see the 'Materials and Methods' section).

Figure 3:
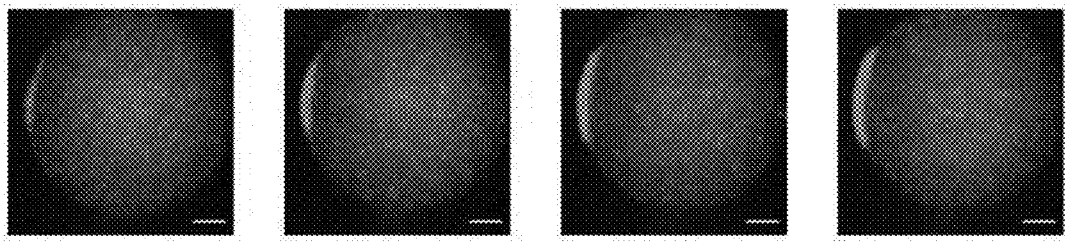
FIG. 3 is a micrograph showing the time lapse images of an experiment of magnetic sorting. Two populations in the droplet: mCherry-*E. coli* mineralized with 3 mM of iron II and non-magnetic EmGFP-*E. coli* (1:5). From the left to the right, the time points are 0, 30, 60.90 min. Scale bar, 60 μm.

Time-lapse observations showed that within few minutes the biomineralized bacteria began to move in a direction oriented towards the magnet, whereas non-mineralized one did not display any net motion (FIG. 3). Moving bacteria eventually accumulated on the edge of the droplet as illustrated by the strong enhancement of mCherry signal intensity (FIG. 3). During this process, non-mineralized bacteria (EmGFP expressing bacteria) remained uniformly distributed within the droplet. After 180 min almost all bacteria were attracted (FIG. 3).

Figure 4:
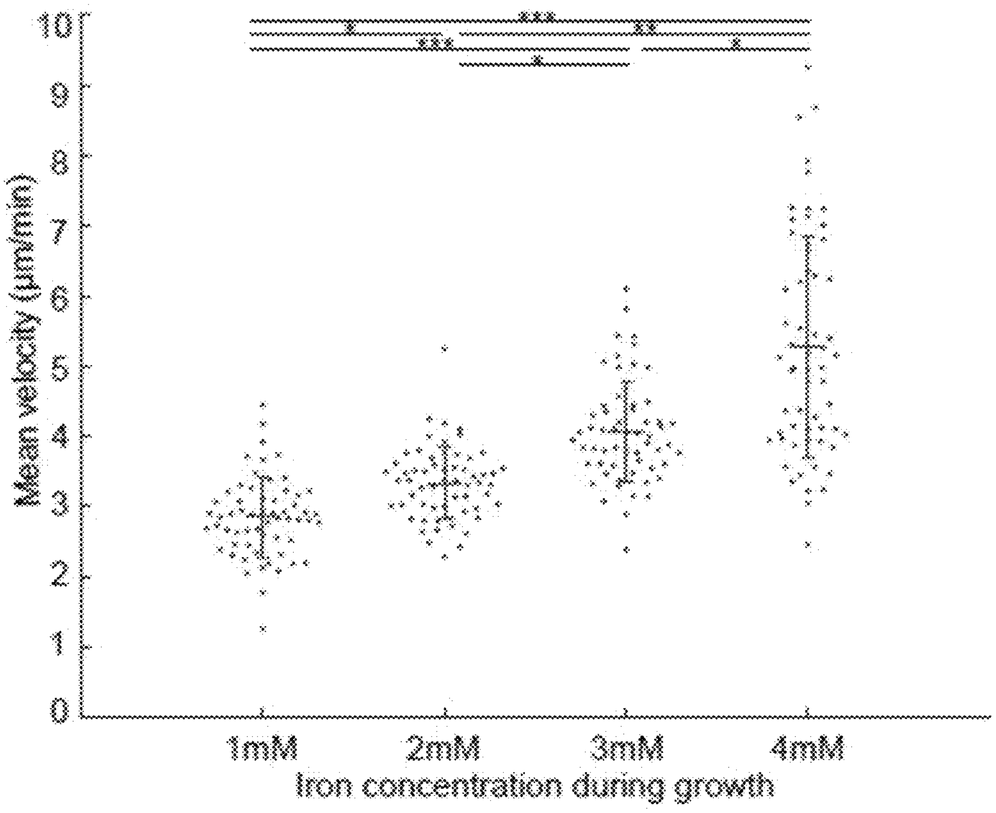
FIG. 4 is a histogram of bacterial speed during magnetophoresis experiments as a function of iron concentration (expressed in mM) during biomineralization. For each condition, the mean+/−standard deviation are displayed, for two independent experiments. 1 mM: 2.85+−0.56 μm/min; 2 mM: 3.34+−0.51 μm/min; 3 mM: 4.07+−0.72 μm/min; 4 mM: 5.26+−1.58 μm/min. $^{*}p<10^{-5}$, $^{}p<10^{-10}$, $^{*}p<10^{-15}$.

In order to quantify the mobility of the mineralized bacteria, we tracked single bacteria trajectories within the droplet and computed their speed. This procedure was performed for respectively 1, 2, 3, and 4 mM iron ($Fe^{2+}$) added during the biomineralization step. For instance, single bacteria that were mineralized with 4 mM iron displayed a directed motion towards the magnet position with a mean speed of about 5.3+/−1.6 μm/min (mean+/−SD) (FIG. 4). We found that the mean speed is roughly linearly correlated with iron concentration loading (FIG. 4).

This asymmetrical magnetic concentration procedure can be applied to force the co-localization of two bacterial populations: EmGFP and mCherry magnetized bacteria can strongly be concentrated within the same area at the vicinity of the magnet.

Altogether, these data showed that MagEcoli bacteria can be spatially manipulated upon magnetic forces, with an efficiency that increases with the concentration of iron added during the biomineralization step. The magnetic concentration process is very specific to the state of biomineralization of the bacteria and did not affect non-magnetized bacteria diffusing in the mixture, allowing to perform basic operations such as magnetic separation and magnetic mixing.

2.3—Becoming of MagEcoli Over Time: How Magnetic Properties Propagate Through Cell Division?

Obtaining magnetized bacteria that can sustain cell division is of primary importance for basic understanding and to envision applications requiring magnetic manipulations of bacteria in a complex environment after hours or days. To examine the transmission of magnetic properties after cell division, we combined microscopy observations and magnetophoresis.

First, we monitored mineralized bacteria growth diluted into fresh LB medium lacking iron supply using optical density measurements. Next, we observed single bacteria that were confined between a coverslide and an agarose pad at various growth stages: before new growth, after 1, 2 and 3 divisions respectively. As the bacteria grew in absence of IPTG, mCherry fluorescence was directly correlated with the presence of magnetic ferritins which allowed us to monitor the becoming of iron oxide ferritin-enriched bodies (FIG. 5).

Figure 5:
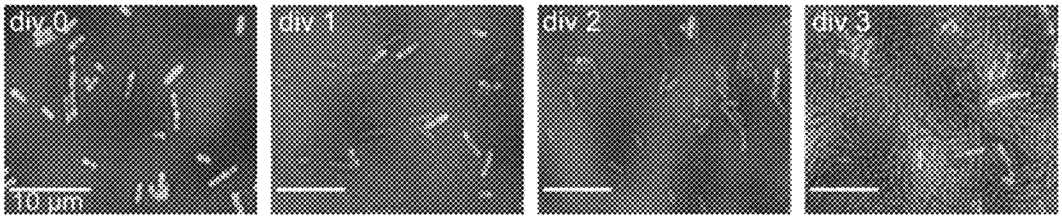
FIG. 5 is a photograph showing the superposition of fluorescence and bright field images of mineralized bacteria after 0, 1, 2, and 3 divisions. Scale bar, 10 μm.
Figure 6:
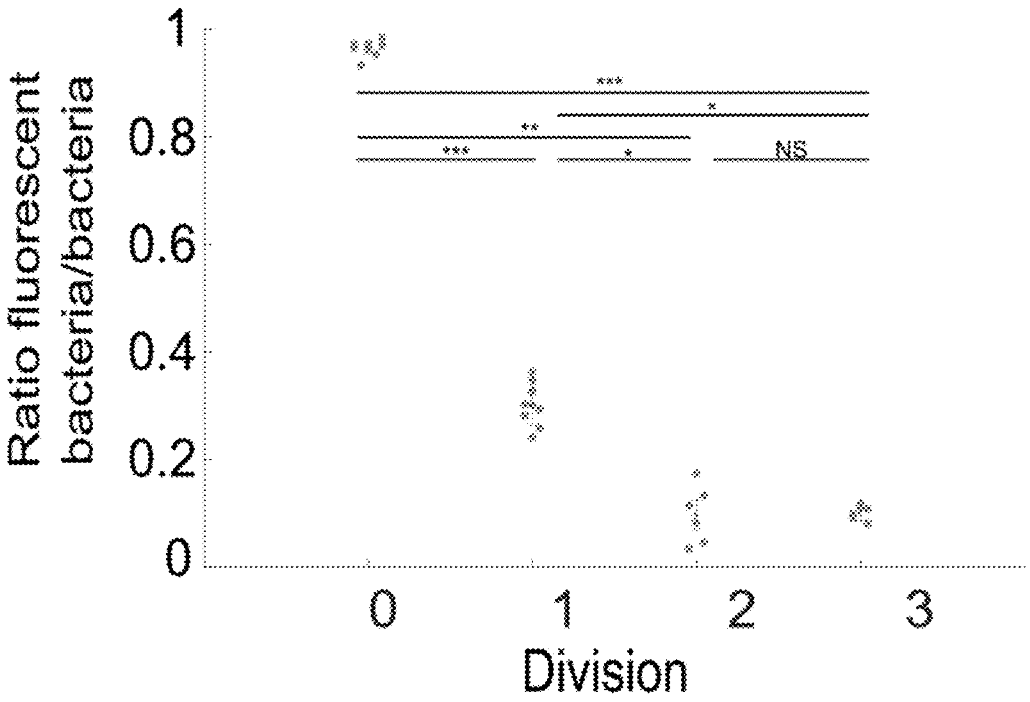
FIG. 6 is a plot showing the quantification of the ratio of still containing mCherry-ferritin bacteria above all bacteria as a function of cell generation. Measures are counted on about 1,000 bacteria, on two different experiments performed at different days. Each point represents a ratio calculated on a picture. Div stands for division. The mean+/−standard deviation are displayed. Div. 0: 0.97+/−0.01, Div. 1: 0.30+/−0.04, Div. 2: 0.10+/−0.03; Div. 3: 0.10+/−0.01. $^{*}p<10^{-10}$, $^{}p<10^{-10}$, $^{*}p<10^{-5}$.

Before division, almost 100% of bacteria displayed mCherry fluorescence reporting the presence of enriched ferritins within their bodies (FIG. 5). Bacteria displayed large inclusion bodies at one or two poles coexisting with a diffuse fluorescence distributed within the bacteria body, in agreement with the TEM assays, and confirming the hypothesis of the strong accumulation of mineralized ferritin at the extremity of the bacteria. For the following images, at 1 to 3 divisions, there was a reduction of the number of bacteria displaying fluorescent ferritins as a function of cell division. After the $1^{st}$ division, nearly 70% of the observed bacteria did not display fluorescent accumulation; and this number increased after 2 and 3 divisions (FIG. 5). In contrast the remaining fluorescence bacteria continue to display a strong ferritin accumulation. This confirmed the hypothesis of an asymmetrical division of the magnetic bacteria that transmit their iron oxide ferritin-enriched bodies to only one daughter cell. We found that about 10% of bacteria conserved a strong concentration of magnetic ferritins in their cytoplasm after 3 divisions—which is in agreement with an asymmetrical cell division model (FIG. 6).

To further document this aspect, we monitored the spatial accumulation of mineralized bacteria after 1, 2, and 3 rounds of cell division as reported by bacterial density measurements.

Figure 7:
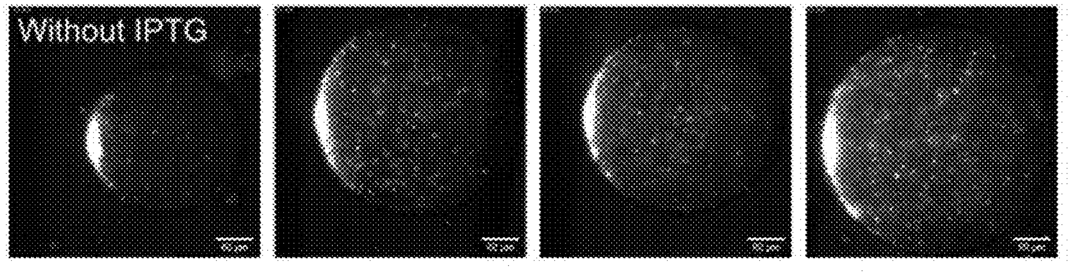
FIG. 7 is a photograph showing the magnetophoresis images of accumulation of mineralized bacteria after 0, 1, 2, and 3 divisions (from the panel to the right), for growth without IPTG. mCherry fluorescence corresponds only to mineralized ferritin. Images are taken after 89 min of accumulation, magnet on the left, scale bar, 60 μm.

First, to determine if there was still a population of magnetic bacteria containing the mineralized ferritin after cell division, new growth of freshly mineralized *E. coli* was performed in a free IPTG medium. Thus, only bacteria displaying mineralized ferritins could be visualized by mCherry fluorescence (FIG. 7). Based on the hypothesis that the division is asymmetrical, we corrected the density inside the droplets to concur with the assumed-remaining fraction of magnetic bacteria. The observations by microscopy showed strong fluorescent bacteria inside the droplets with a density quite similar for the different division steps, as expected. Moreover, fluorescent bacteria still strongly accumulate towards the magnet even after 3 divisions, again in agreement with the asymmetrical division model (FIG. 7).

Figure 8:
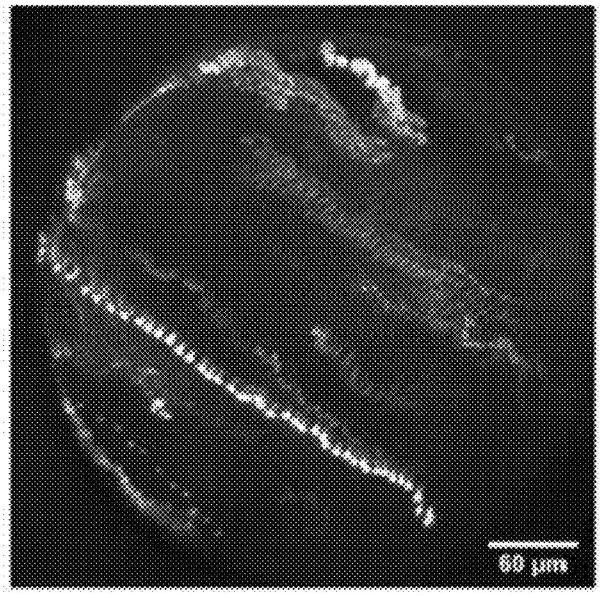
FIG. 8 is a micrograph showing the projection of trajectories over 49 minutes of mineralized bacteria after 24 hours of growth. Scale bar, 60 μm.

Then, to assess if we could use MagEcoli on the long term, we observed the mineralized bacteria after 24 hours of growth (FIG. 8). We found that the remaining fluorescent bacteria were attracted in directed fashion upon magnetic forces. They could be attracted with a mean speed of about 4.9 μm/min (N=15 tracked trajectories total, 3 different assays)—whereas the mean speed of mineralized bacteria that did not undergo any cell division were found to be about 5 sm/min. This proved that after at least 10 divisions or more (minimal estimation after 24 hours), MagEcoli kept the majority of their magnetic properties.

Figure 9:
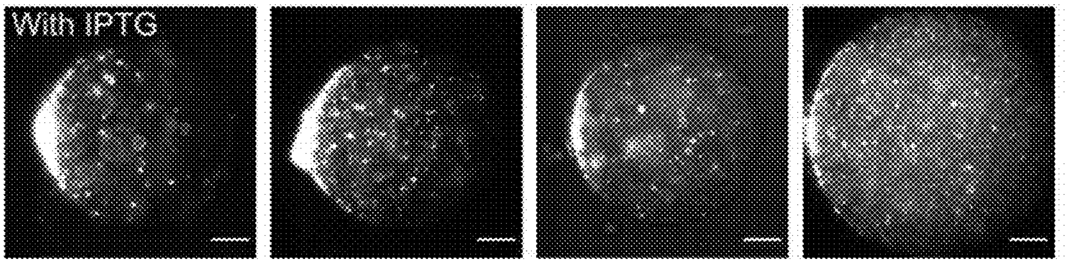
FIG. 9 is a micrograph showing the magnetophoresis images of accumulation of mineralized bacteria as a function of the division step (0, 1, 2, and 3 divisions—from the left to the right) in a medium supplemented with IPTG. All bacteria express mCherry fluorescence. Images are taken 89 min after applying the magnetic forces, magnet on the left, scale bar, 60 μm.
Figure 10:
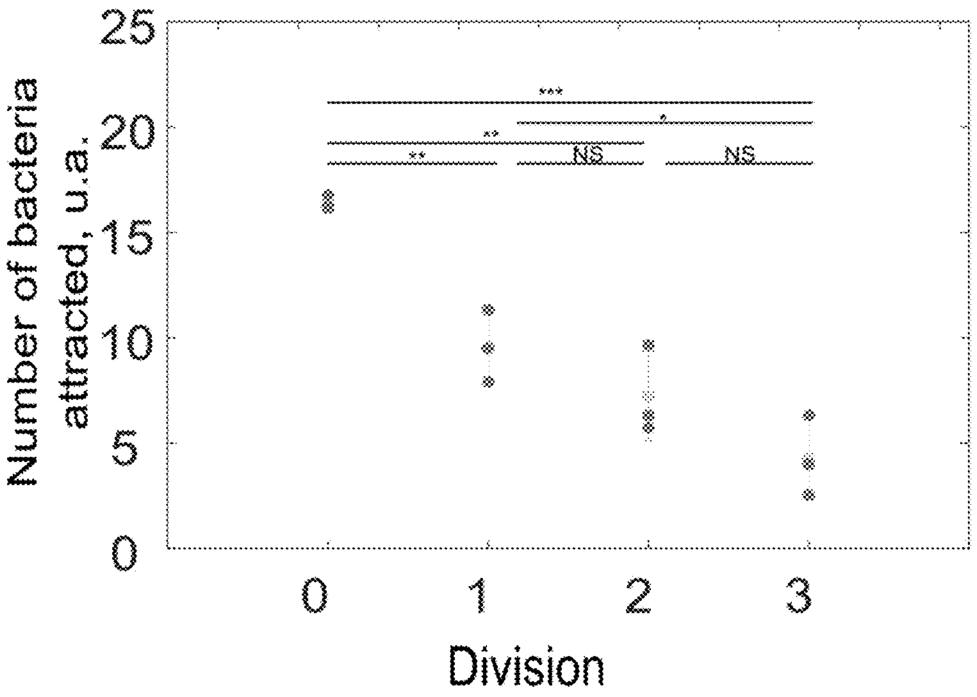
FIG. 10 is a plot showing the quantification of the number of bacteria attracted towards the magnet for the corresponding experiment (displayed in FIG. 9). The integrated density of a region of interest towards the magnet was monitored at 89 minutes and normalized by the integrated density of the whole droplet at 0 minute. For each condition, the mean+/−standard deviation are displayed, for three independent experiments. Div. 0: 20 16.37+/−0.34; Div. 1: 9.57+−1.71; Div. 2: 7.23+−2.13; Div. 3: 4.28+−1.91. $^{*}p<0.1$, $^{}p<0.01$, $^{*}p<0.001$.

To go further, we repeated the magnetophoresis assays with bacteria that grown in a medium supplemented with IPTG—to allow all the bacteria to be monitored by fluorescence (FIG. 9). The microscopy images showed that all bacteria displayed m-Cherry fluorescence as expected. Yet, during the magnetophoresis, we found that the fraction of magnetized bacteria towards the magnet decreased as a function of the division step: 16.4+/−0.3, 9.6+/−1.7, 7.2+/−2.1, 4.3+/−1.9 (arbitrary units) for division 0, 1, 2, 3 respectively (N=3 independent mineralization). The results showed that the ratio of mCherry-fluorescent bacteria attracted toward the magnets decreases with bacterial generations (FIGS. 9 and 10), in agreement with the previous experiments.

Altogether, these data showed that the mineralized bacteria are still able to divide after biomineralization. Moreover, a proportion of MagEcoli keep their magnetic properties through cell division. The conservation of magnetic properties through division is due to the asymmetrical transmission of iron oxides ferritin-enriched bodies to daughter cells. In contrast in the case of symmetric divisions (e.g. absence of clusters of iron oxides ferritin-enriched bodies), we will expect a strong dilution of the magnetic properties at each cell cycle with a reduction of about 10-fold after 3 generations.

2.4—Sensitive Detection by Magnetic Concentration of MagEcoli

Figure 11:
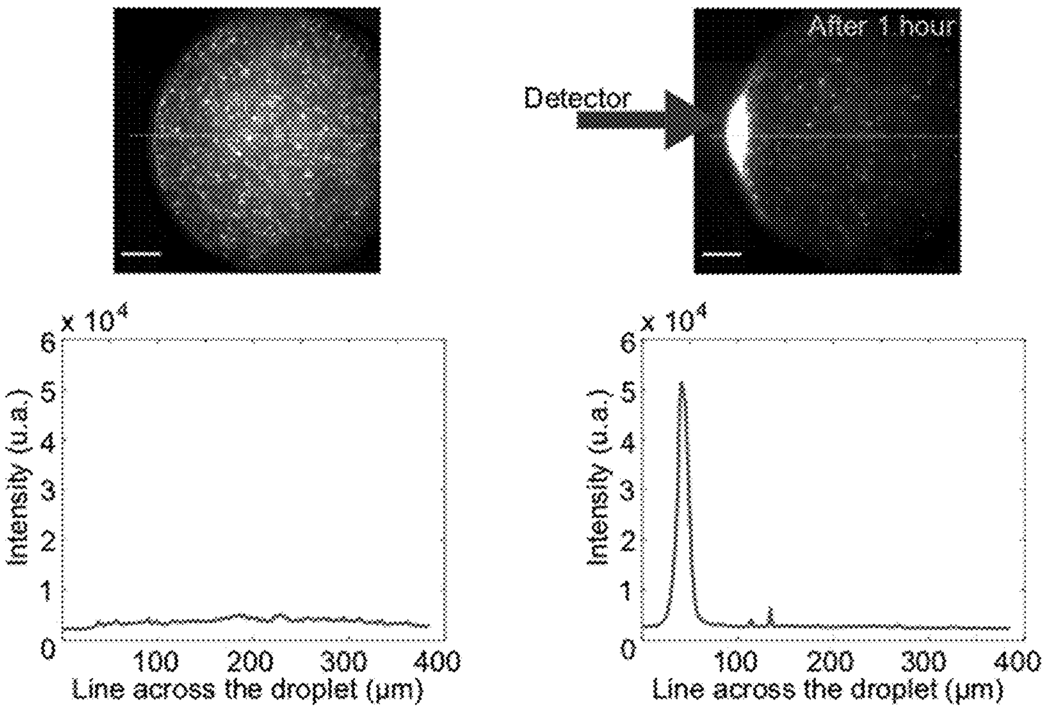
FIG. 11 represents micrographs and plots illustrating the concentration increase of magnetic bacteria upon magnetic force application. On the left panel: micrograph of 4 mM mineralized bacteria at t=0 min (upper panel). Scale bar, 60 μm. The intensity of mCherry signal on the line across the droplet is represented in the plot (lower panel). On the right: photograph of 4 mM mineralized bacteria after two hours (t=120 min). Scale bar, 60 μm. Same illumination set-up. The intensity of mCherry signal on the line across the droplet is represented on the plot (lower panel).

In the context of applications dedicated to the detection of pathogenic bacteria or pollutant, we aimed to increase the sensitivity of the detection by triggering a strong enhancement of the biosensor concentration at a specific spatial position (FIG. 11). In order to facilitate the manipulation and observation of the magnetic bacteria, the mixture was first encapsulated in small compartments made of water-in-oil droplets (50 μm to 800 μm) generated by performing an emulsion of bacteria dispersed in oil. A gradient of magnetic field is produced by a permanent magnet (NdFeB magnet) positioned at a distance ranging from 500 to 800 μm from the droplets. This geometry is very suitable for single point detectors: portable device for field studies or detection in confined droplets in a geometry very well suitable to microfluidic set-up (lab-on-a-chip assay).

2.5—Example of Detection: Using MagEcoli to Detect Chemicals Produced by Bacteria In the idea of using our MagEcoli as a spatially manipulated biosensor, we decided to implement our system of magnetic bacteria. As bacterial pathogens produce specific signaling molecules, such as Acyl Homoserine Lactone (AHL), that are the basis of cell-cell communication, we wanted to demonstrate that MagEcoli are able to detect a low dose of such signaling molecules, thus inferring the presence of living pathogenic bacteria.

Figure 12:
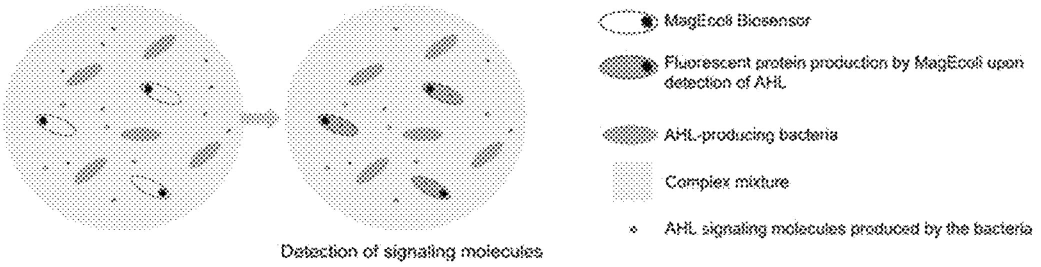
FIG. 12 is a schematic representation of the principle of MagEcoli sensing strategy. An AHL-sensitive promoter plasmid is inserted in MagEcoli to sense AHL molecules produced by AHL-producing bacteria. Upon AHL uptake, MagEcoli produces a fluorescent protein.

To do so, we programmed MagEcoli to detect N-(β-ketocaproyl)-L-Homoserine lactone (a type of AHL molecules) by producing red fluorescent proteins (mRFP1). For this purpose, we inserted AHL-sensitive promoter plasmid in EmGFP-ferritin expressing bacteria (FIG. 12). We performed the biomineralization of the EmGFP-ferritin expressing bacteria modified with the AHL-sensitive plasmids. We found that the bacteria retained their capacity to be attracted by a magnet. Next, we mixed AHL-sensing MagEcoli with a second bacterial population that produce AHL (AHL-producing bacteria). Both populations expressed a green fluorescent signal as confirmed by epifluorescence observations.

Figure 13:
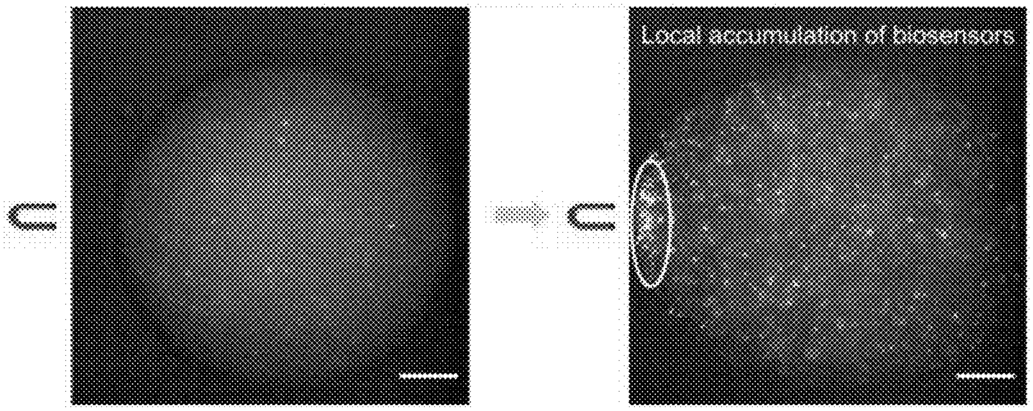
FIG. 13 represents micrographs of AHL-sensing MagEcoli in presence of AHL-producing bacteria. Left panel: micrograph of the fluorescence intensity emitted by MagEcoli at initial time (0 min). Right panel: After 119 min magnetic attraction, MagEcoli emitting red fluorescence signal locally accumulate at the vicinity of the magnet, reporting of AHL compounds. Scale bar, 60 μm.

We performed magnetophoresis experiments as previously described and found an increase of EmGFP signal accumulating near the magnet and corresponding to the magnetic attraction of the AHL-sensing MagEcoli. After 2 hours almost all the sensors were spatially localized, in agreement with the previous magnetophoresis assays. Alongside, we detected an increase of red fluorescence in the droplets after 90 minutes, indicating the production of mRFP1 upon induction with AHL. This mRFP1 signal was also strongly colocalized with the GFP fluorescence at the vicinity of the magnet (FIG. 13). This indicates that the magnetic bacteria were able to detect the presence of AHL in the droplet and simultaneously were migrating toward the magnet. The accumulation of bacteria toward the magnet allow to increase the mRFP1 signal reporting of AHL compounds.

These data show that our modified bacteria retain their capacity to be biochemical active and can be programmed as biosensors to detect bacteria.

2.6—Production and Release of Molecules at the Micrometric Scale by Localized Magnetic bacteria Confined in Droplets To envision applications related to the use of MagEcoli as a molecule-delivery vehicle, we need to demonstrate that MagEcoli bacteria could secrete specific molecules while keeping their capacity to be manipulated by a magnetic field.

As a proof-of-concept, we engineered MagEcoli to produce N-(β-ketocaproyl)-L-Homoserine lactone, an AHL molecule, and we used a second population of bacteria to detect the produced AHL. To do so, we inserted, in EmGFP-ferritin expressing bacteria, the plasmid coding for the production of AHL.

Figure 14:
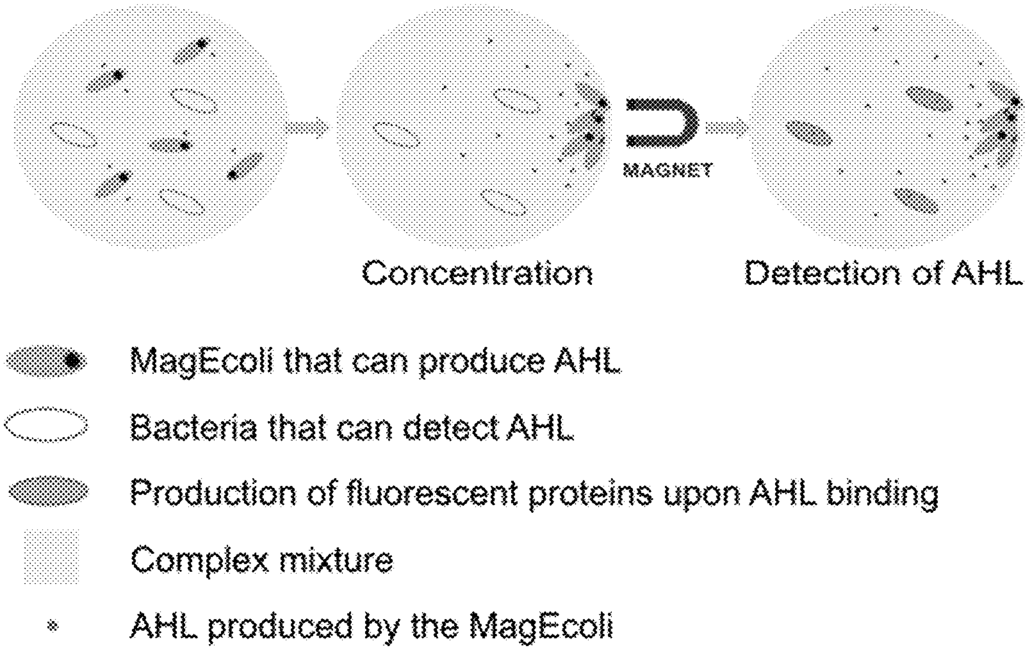
FIG. 14 is a scheme of the spatial localization of MagEcoli producing AHL molecules. Produced AHL molecules is detected by a second population of non-magnetic bacteria that express mRFP1 as a function of AHL concentration.
Figure 15:
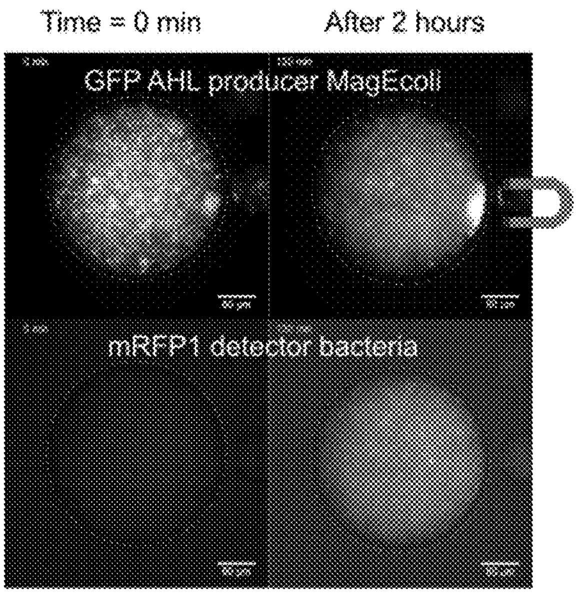
FIG. 15 represents micrographs of experiments consisting in the spatial localization of MagEcoli producing AHL molecules (referring to the schematic representation depicted in FIG. 14). GFP and mRFP1 signals of bacteria in droplets containing green AHL-producer MagEcoli and AHL bacteria sensors acquired at 0 min (left column); and 119 min (right column). Scale bar, 60 μm.

The AHL sensing bacteria were non-mineralized strain transformed with AHL-sensitive promoter plasmids previously described (FIG. 14). After the biomineralization of the AHL-producing bacteria, we mixed the two populations in droplets and performed magnetophoresis. At t=0, we observed the homogenous distribution of AHL-producing MagEcoli (EmGFP) in the droplets. Over time, EmGFP-MagEcoli started to accumulate toward the magnet (a strong accumulation appeared at t=30 minutes) that coincided with the uniformly increased of mRFP1 fluorescence inside the droplets (after one hour) (FIG. 15). This showed that we were able to attract in space the MagEcoli and that they were enough biochemically active to express the AHL molecule as expected. This demonstrates that MagEcoli can produce specific molecules (they are still biochemically active), which might be of interest for future perspectives including the spatial control of drug release.

Figure 16:
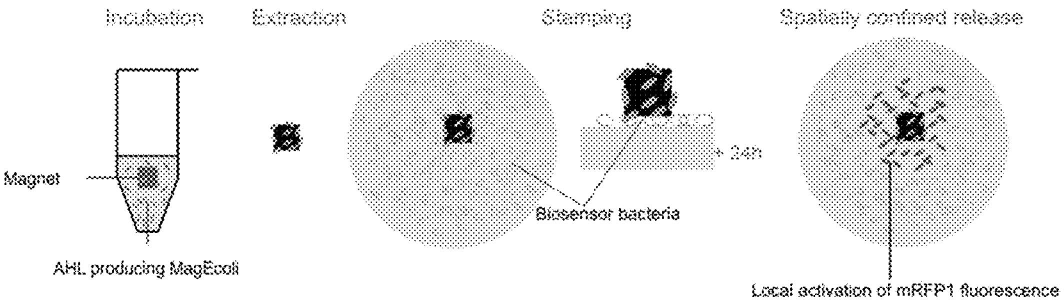
FIG. 16 is a scheme of strategy used to generate a spatial patterning of cell communication on solid surface mediated by contact printing of pre-sorted AHL-producer magnetic bacteria. AHL-producing MagEcoli were sorted from a liquid medium with a magnet and deposited on a solid medium made of agar gel, thus leading to obtain AHL-producing MagEcoli confined between the magnet and the agar-pad. The agar-pad solid medium displays another population of bacteria that will produce mRFP1 protein upon interaction with AHL diffusing molecules.
Figure 17:
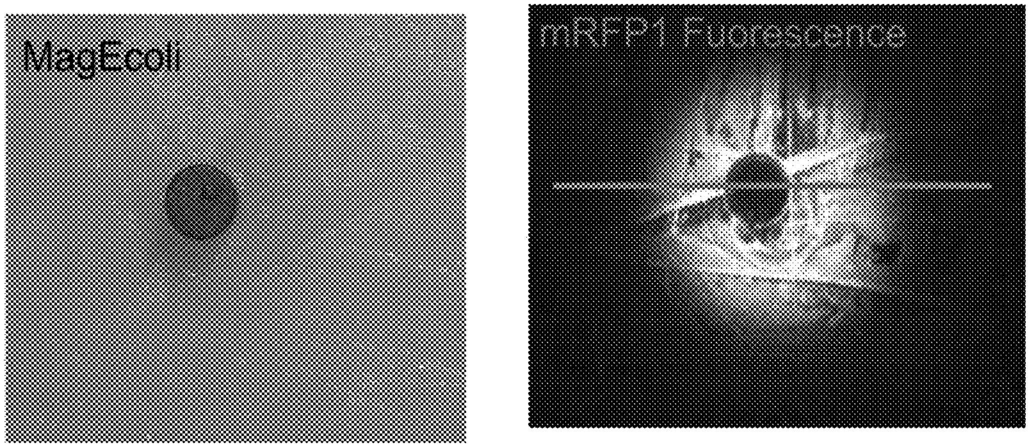
FIG. 17 represents photographs of the experiments depicted in FIG. 16. Left: photograph of an agar gel acquired 24 hours after the deposition of the magnet. Bright field. Right: mRFP1 fluorescence reporting the detection of AHL molecules.
Figure 18:
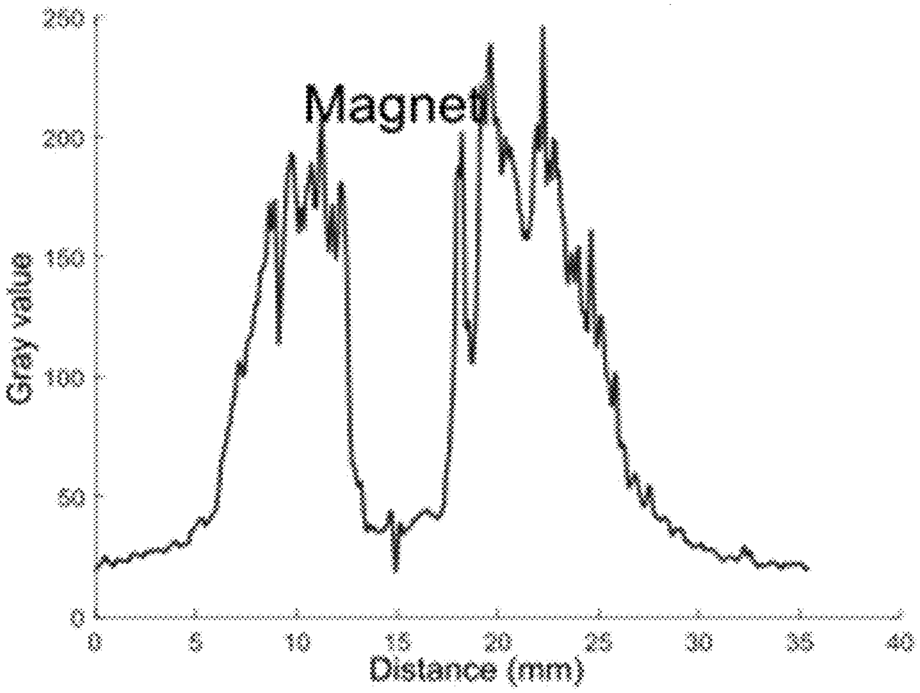
FIG. 18 is a plot profile of the intensity of the mRFP1 fluorescence across the line depicted in the right photograph in FIG. 17.

2.7—Spatial Patterning of Cell Communication on Solid Surface Mediated by Contact printing of Pre-Sorted AHL-Producer Magnetic Bacteria Here, we demonstrated that we could sort AHL-producing MagEcoli from a liquid medium and transfer the bacteria population on an agar surface via stamping/contact-printing. As a proof-of-concept, we designed an assay in which we extracted MagEcoli, then deposited them on a solid surface on a specific surface area to spatially constrain the source of production of specific chemicals (e.g. AHL). We first collected the AHL-producing MagEcoli using a magnet and subsequently deposited the magnet on a solid medium made of an agar gel to obtain AHL-producing MagEcoli confined between the magnet and the agar surface (FIG. 16). Prior to this step, an AHL-sensing bacteria population was initially deposited on the agar-surface. Interestingly, we could detect a spatial gradient of intensity of mRFP1 production localized at the vicinity of the magnet 24 hours after depositing AHL-producing MagEcoli. This demonstrated that AHL-producing MagEcoli were still active and that AHL molecules diffused away which resulted in activating a spatial pattern of mRFP1 production (FIGS. 17 and 18).

2.8—Capture and Spatial Attraction of Targeted Bacteria by Antigen/Antibody Recognition Besides, in the context of whole cell biosensors, we engineered MagEcoli to capture and trap a specific cell (here a bacterium) in order to manipulate, concentrate in space, and/or sort the targeted cells. We used MagEcoli as surface display of nanobodies and antigens.

Figure 19:
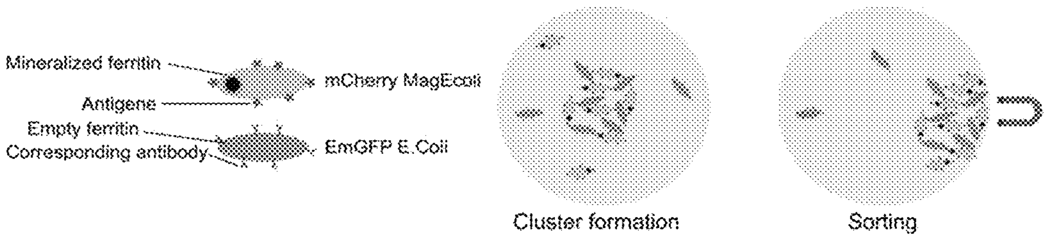
FIG. 19 is a scheme of the assay of the capture and spatial attraction of targeted bacteria by antigen/antibody recognition. Green nanobody-expressing bacteria are the target of red antigen-expressing MagEcoli.
Figure 20:
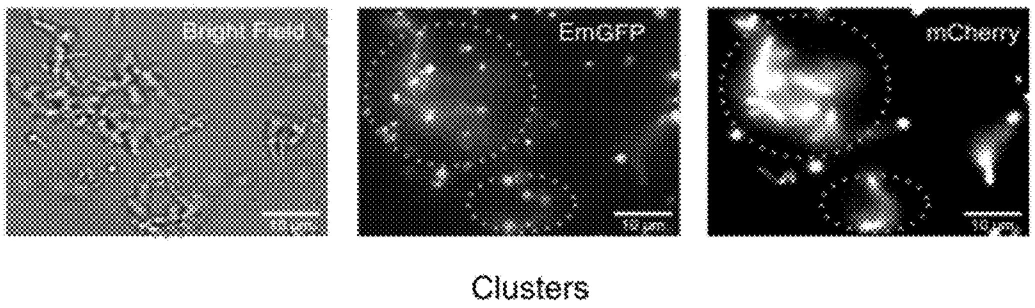
FIG. 20 represents micrographs showing mixed clusters of mCherry-MagEcoli displaying antigen on their surface adhering with EmGFP-ferritin expressing *E. coli* displaying the corresponding nanobodies (epifluorescence observations). Scale bar, 10 μm.

MagEcoli were transformed to express on their outer membrane an antigen or the corresponding nanobody. For this, we inserted in fluorescent-ferritin expressing bacteria the plasmid coding for the antigen or the corresponding nanobody respectively (FIG. 19). Then, we checked that antigen-expressing MagEcoli were able to adhere on nanobodies displayed on ferritin-expressing bacteria. To trigger the expression of antigens and nanobodies we cultivated our bacteria in presence of anhydro tetracycline. With this antibiotic only, we observed on fluorescence microscopy large clusters of red and green bacteria (FIG. 20). This indicated that MagEcoli were able to produce other proteins and aggregates with each other.

Figure 21:
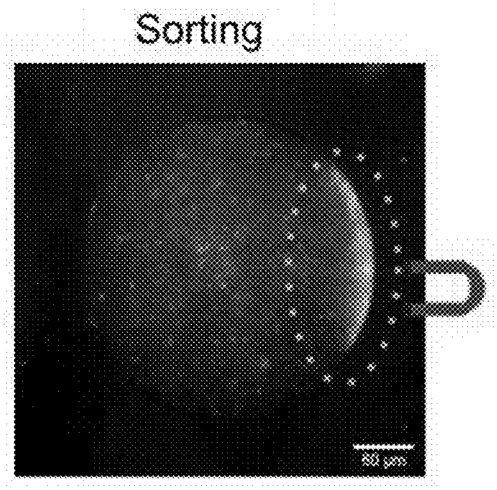
FIG. 21 is a micrograph showing the accumulation of antigen-producing MagEcoli (red) and the nanobodies-producing ones (green). Epifluorescence observations were performed after 120 minutes upon magnetic field application. Scale bar, 60 μm.

Next we assessed if the antigen-expressing MagEcoli can be manipulated by mixing in a droplet the two populations of bacteria: the antigen-producing bacteria (red) and the nanobodies-producing ones (green). We found an accumulation of both populations of bacteria toward the magnet (FIG. 21). As only the red ones were mineralized, these data proved that MagEcoli, with the system of antigen/nanobody, were able to capture targeted bacteria and to locally accumulate them in space.

These data demonstrate that MagEcoli may be designed to specifically recognize pathogenic bacteria, other microbes of interest, or mammalian cells displaying specific surface markers (cancer cells).

2.9—Spatial Modulation of Cell Invasion by MagEcoli

As additional proof-of-concept of spatial control of magnetic bacteria, we devised an assay to monitor and quantify the spatial localization of bacterial invasion on human cell culture. We focused on invasin proteins from *Yersinia pseudotuberculosis* as an output module that enables *Escherichia Coli* to invade cancer-derived cells such as HeLa cells.

To do so, we co-transformed *E. coli* with a plasmid coding for an invasin and for the EmGFP-ferritin. The genetically modified bacteria should be able to be magnetized, tracked by fluorescence and to enter into cells.

First, we validated that our bacteria with only EmGFP-ferritin were unable to invade cells and that the bacteria co-expressing both invasin and EmGFP-ferritin could enter into cells. We also found that MagEcoli modified to display invasin proteins on their outer membrane can specifically recognize and invade HeLa cells (FIG. 9A)—thus demonstrating that our invasin-expressing MagEcoli can mimic the entry mode of infectious bacteria into cells, which can be envision as a first step before releasing a cytotoxic agent into invaded cancerous cells.

Figure 22:
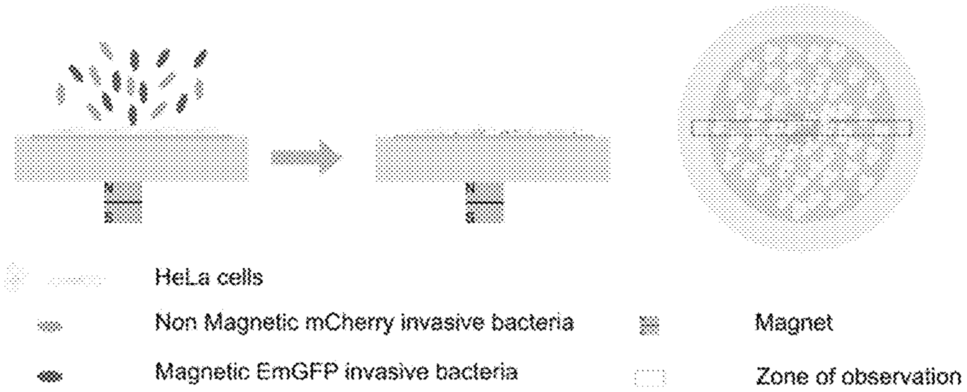
FIG. 22 is a schematic representation of the assay used to quantify the spatial control of invasion on human cell culture using magneto-localization of MagEcoli. Invasin-expressing MagEcoli placed on a culture dish with HeLa cells.
Figure 23:
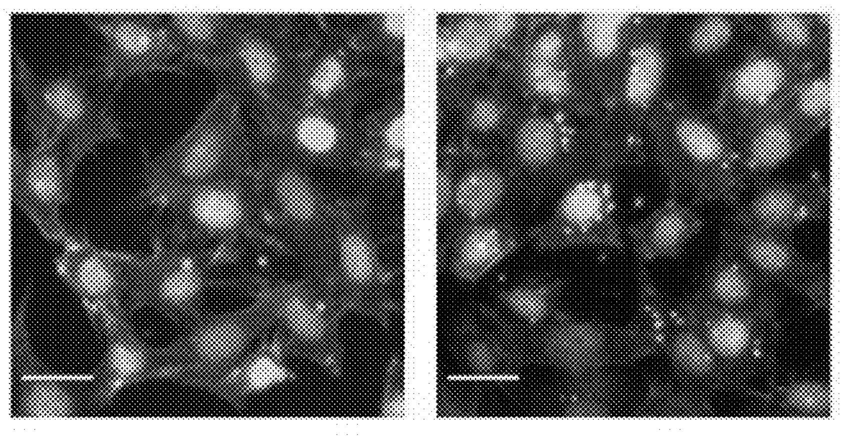
FIG. 23 corresponds to micrographs of the invasion of Hela cells by invasive MagEcoli (following the schematic representation depicted on FIG. 22). Left panel shows bacteria invasion far from magnetic field. Right panel shows a strong enrichment of HeLa infection by MagEcoli at the vicinity of the magnetic field localization. Epifluorescence observations. Scale bar, 60 μm.

We next monitored invasion as a quantitative readout to measure the link between spatial localization, local magnetic enrichment of bacteria, and infection efficiency in HeLa cells. We designed an assay to spatially control and enhance bacterial invasion into cells. We covered a cell culture dish containing HeLa cells with infectious MagEcoli in a PBS medium whose density was adjusted to prevent sedimentation. We left the cells in contact with the bacteria for 4 hours with a magnet under the dish (FIG. 22). After infection, we washed to remove the bacteria that had not entered into cells. Then, we stained the cells (F-actin, nucleus) and observed bacteria/HeLa colocalization using fluorescence microscopy. The triplicated assays indicated that the magnetic bacteria (expressing EmGFP-ferritin and invasin) have invaded cells and can be found near the nucleus. Strikingly, the cells in the presence of the magnetic gradient contained in their cytoplasm way more bacteria than the one without magnetic field, indicating an influence of magnetic attraction on the rate of infection (FIG. 23).

Figure 24:
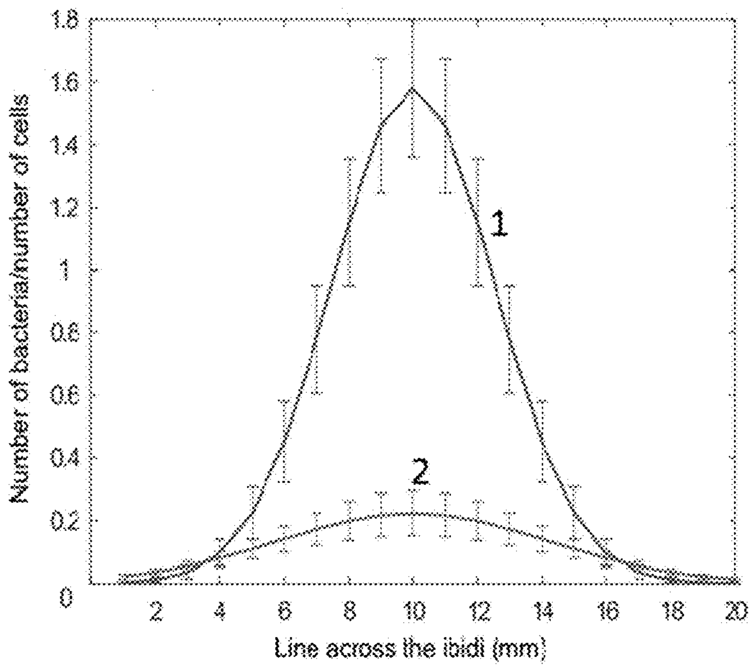
FIG. 24 is a plot showing the quantification of the number of bacteria per cell as a function of localization along the magnetic field accumulation. Curve 1 represents the mean value of the number of magnetic bacteria per cell; Curve 2 represents the mean value of the number of non-magnetic bacteria per cell. The abscissa represents the zone of observation, in millimeter. The data are normalized by the number of cells counted on each field of observation.

To quantify the rate of infection, we counted the number of bacteria entered in cells in the presence or in the absence of magnetic field. For the cells next to the magnet, the invasion of cells was at least 8 times increased in regards as in its absence. An internal control with non-mineralized *E. coli* expressing both mCherry-ferritin and invasin confirmed that this result was mainly due to the magnet and not to geometry of the system (FIG. 24).

Altogether, these data showed that invasive MagEcoli were enough metabolically active to co-express a membrane protein (here invasin) and to enter into cells after biomineralization. The magnetic forces were sufficient enough to generate a concentration increase of MagEcoli resulted in forcing the contact with bacteria and cells in order to increase the rate of infection in a spatial controlled manner. This proof-of-concept experiment allows to envision several applications including the spatial control of magnetic bacteria programmed as molecule-delivery vehicles inside living human cells, which can be used to modify cell fate or trigger cell death (cancer cells).

2.10—Extraction of In Vivo Mineralized Ferritins

Here we aimed in using MagEcoli as a living factory enabling the production of functionalized and monodisperse magnetic ferritin nanoparticles in a single step. This approach is different from current studies that produce ferritin-based nanoparticles using purified apo-ferritins and that require to perform a second mineralization in test tubes (see, e.g., Tatur and Hagen, *FEBS Letters,* 2005, vol. 579 (21):4729-4732; Tatur et al., *Extremophiles,* 2006, vol. 10(2): 139-148).

We first designed an assay that consisted in extracting biomineralized ferritins from MagEcoli. We designed two plasmids that led for the production of ferritin nanocages in which each monomer is fused in N terminal with a fluorescent protein (EmGFP or mCherry, for visualization), with a FRB or FKBP protein, and 6 His-tag (for purification). FRB/FKBP system allows to use chemically-inducible dimerization method to enable the formation of micrometric clusters of ferritins with addition of rapamycin, thus possibly enhancing the magnetic properties of the nanoparticles (see the "Materials and Methods" section, plasmids called pET28duet-FKBP-mCherry-ferritin_FRB-EmGFP-ferritin or pET28duet-FRB-EmGFP-ferritin_FKBP-mCherry-ferritin). After induction of proteins and biomineralization, we lysed the bacteria and purified by affinity the proteins of interest. We characterized the concentration of the proteins with Nanodrop measures, Bradford assay, and SDS page gel.

Figure 25:
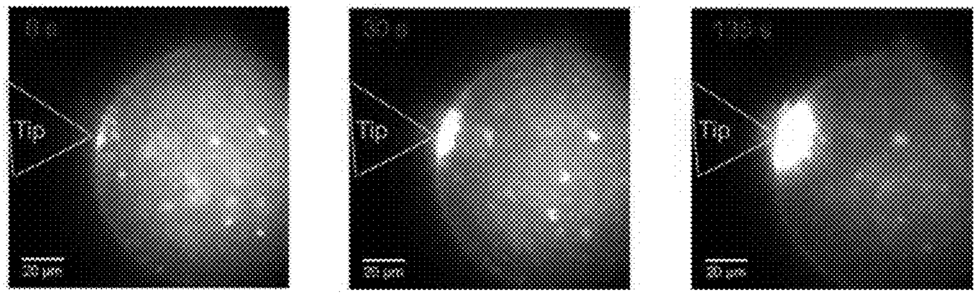
FIG. 25 represents micrographs of the magnetic attraction of clusters made of purified FRB-EmGFP ferritins dimerizing with FKBP-mCherry-ferritins. First, bacteria expressing FRB-EmGFP-ferritins or FKBP-mCherry-ferritins were mineralized. Second, the ferritin fusions were extracted and specifically purified. To demonstrate that FRB and FKBP fusion proteins remained functional, we next assessed if FRB-EmGFP-ferritins or FKBP-mCherry-ferritins could interact upon triggering their heterodimerization using rapamycin. Because of the multivalency of ferritin assemblies, this allowed to trigger the formation of micrometer size clusters of ferritins. A magnetic tip was used to attract the magnetic ferritins. mCherry channels are observed at 0, 30 and 135 s (from left to right). Scale bar, 20 μm.

To demonstrate that FRB and FKBP fusion proteins remained functional, we next assessed if FRB-EmGFP-ferritins or FKBP-mCherry-ferritins could interact upon triggering their heterodimerization using rapamycin. Because of the multivalency of ferritin assemblies, this allowed us to trigger the formation of micrometer size clusters of ferritins. With a ratio 1:1 between purified FRB-EmGFP-ferritins or FKBP-mCherry-ferritins, we observed in the droplets apparition of micrometric clusters (FIG. 25, left panel (t=0)). To monitor the magnetic properties of the purified mineralized ferritin clusters, we devised a set-up of magnetophoresis using a magnetic tip to generate high magnetic field gradient ($10^4\ T \cdot m^{-1}$). With the magnetic tip, we instantaneously monitor a strong attraction of clusters of ferritin proteins at its vicinity (FIG. 25).

These data indicated that we can extract mineralized ferritins from MagEcoli that are magnetic and display a specific functionalization (with a fluorescent or protein interacting tag).

The production of nanomaterials from microorganisms provides several remarkable features such as the very high yield of production; low cost; and the possibility to scale-up the production process using large bioreactors optimized for industrial manufacture. Our approach could also impact the cost of production and purification that is often a bottleneck in the industrial production of high value compounds. In addition, our process is a first step towards a sustainable (greener) and a bio-based economy.

Example 2

In order to assess whether the magnetic bacteria according to the invention (MagEcoli) could be used for biotechnological purposes, the survival and maintenance of their magnetic properties were assayed in vivo. Their resistance to the intestine of a simple model organism, such as *C. elegans*, was assessed. Then, the effect of MagEcoli on the relaxation times was measured by NMR, in order to evaluate whether it could be good reporter agents for MRI.

1—Materials and Methods 1.1—Strains and Plasmids

The bacteria are Rosetta, SIGMA-ALDRICH® BL21 or MG1655.

For the study with *C. elegans* and the NMR measurements the plasmid used are the one described in example 1. The biomineralization process was the same one as described in example 1.

1.2—Feeding of *C. elegans*

100-200 μL of bacteria were spread at the center of fresh *C. elegans*' petri dish with Kanamycin. A small agar cube with worms was transferred on the dish. *C. elegans* and bacteria were let in contact for 6-24 hours at 20° C., depending on the conditions of the experiment. The worms were collected for observation or lysis in M9 medium.

1.3—Microscopy Observation of Single *C. elegans*

For the observation of *C. elegans* in fluorescence microscopy, the worms were taken out from the plate and put in an M9 medium containing sodium azide. The worms where then deposited on an M9-agar pad containing sodium azide spread on a coverslip. The observations were performed the same day with epifluorescence microscopes.

1.4—Lysis of *C. elegans* and Magnetophoresis

After having fed the *C. elegans* with mineralized bacteria for 24 hours at 20° C., the worms were collected with M9 medium. The worm was deposited on agar dish enriched in gentamicin to remove the external bacteria that might have adhered to the *C. elegans*. The worms were let to crawl in the dish for 30 minutes. Next, the worms were solubilized and collected in M9 medium with 25 mM Levamisole (for immobilization) and 100 μg/mL gentamicin. The samples were kept under agitation for 30 minutes at room temperature. The *C. elegans* worms were washed with M9+100 μg/mL gentamicin first then M9 alone. The lysis was performed by putting the worms in PBS 1× with 0.1% Triton X100. Carbide beads were added to mechanically lyse the worms with the vortex. The supernatant was collected and put aside for magnetophoresis.

1.5—NMR

The mineralized bacteria were washed twice in M9 medium. A M9-agar gel was prepared by diluting 0.3% agarose in M9. The pellet of washed bacteria was mixed with M9-agar and inserted in an NMR tube for measurements.

2—Results 2.1—In Vivo Viability of MagEcoli in *C. elegans*

*C. elegans* was fed with MagEcoli in order to 1) monitor the presence of magnetic bacteria in the digestive tract (or lumen) of *C. elegans*, and 2) to do magnetophoretic experiments on the worms, to assess whether its incorporation in the digestive tract did not affect the magnetic properties.

Because many *C. elegans* worms naturally have a grinder at the entrance of their digestive tract in order to crush bacteria, a grinder defective strain of *C. elegans* was selected.

After a 24-hour incubation of MagEcoli or fluorescent ferritin-producing *E. coli* with worms, the lumen was observed with epifluorescence microscopy. The red fluorescence corresponding to bacteria was diffuse but also let distinguish bacterial bodies along the digestive tract. This indicates that bacteria have not entirely been crushed by the lumen of this particular strain.

After observation by fluorescence of intact MagEcoli inside the lumen of *C. elegans*, an assay was performed to assess whether the bacteria were still magnetic. After a treatment with an antibiotic to remove external *E. coli* and a drug to prevent the worm from digesting the bacteria and expulsing them, *C. elegans* was chemically and mechanically lysed in order to extract the intestinal MagEcoli. Individual bacteria and also large aggregates of organic matter were observed.

Then a magnetophoresis assay was performed on the lysate. With the red fluorescent channel, the trajectory of individual MagEcoli mineralized with 2 mM and 4 mM of iron was assessed. When the trajectories were superposed over time, it could be observed that they longitudinally follow the direction of the magnetic gradients. This means that the bacteria were still attracted toward the magnet; the magnetic properties were unaltered. Therefore, MagEcoli are intact in the lumen and retain magnetic properties.

2.2—NMR Experiments

As iron oxide can be negative contrast agent in MRI (they decrease the relaxation time T2 and increase the other relaxation time T1), the goal was to further determine whether MagEcoli possess these properties. The effect on the relaxation times T1, T2 and T2* (which acts similarly to T2 but depends on the bacterial environment) of MagEcoli was measured by NMR.

Figure 26A:
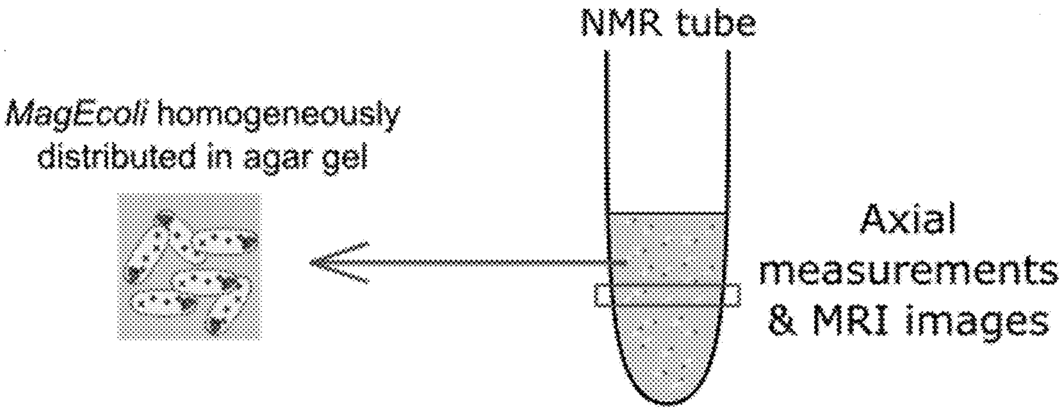
FIGS. 26A, 26B and 26C represent a scheme and graphs illustrating the NMR measurements of MagEcoli in vitro. 26A: The NMR tubes are filled with bacteria entrapped in an agar gel. Axial measurements of T2, T1 and T2* are performed as well as MRI when needed. 26B: The 1/I2 are displayed as a function of the concentration of iron added during biomineralization of bacteria. Squares represent the data for the MagEcoli trapped at an O.D. of around 2-3 in the NMR tube; inverted triangles represent the MagEcoli at an O.D. of around 1. Diamonds represent the 1/T2 measured with control bacteria, that do not overexpress ferritin, at an O.D. of around 1. The triangle represents the signal for LB medium supplemented with 4 mM of iron. Each dot represents a sample. The error bars are calculated by the NMR apparatus. 26C: The graph represents the ½ measured for MagEcoli mineralized with 2 mM of iron as a function of O.D. in the NMR tube. The squares represent the data for the MagEcoli whereas the diamond displays the 1/T2 measured for LB supplemented with 4 mM of iron. Each dot represents a sample. The error bars are calculated by the NMR apparatus.

Different samples of NMR tubes filled with M9-agar were prepared and mineralized bacteria were immobilized. The T1, T2 and T2* were measured for different concentrations of bacteria in the tube (FIG. 26A). It was observed that MagEcoli magnetic bacteria, when mineralized at 4 mM, can be observed with NMR on axial and coronal sections of the tubes. They seemed to have a strong effect on the T2 (they decrease it), and to increase the T1 during the assays. Moreover, the T2* was affected in the same way as the T2 by the bacteria.

Figure 26B:
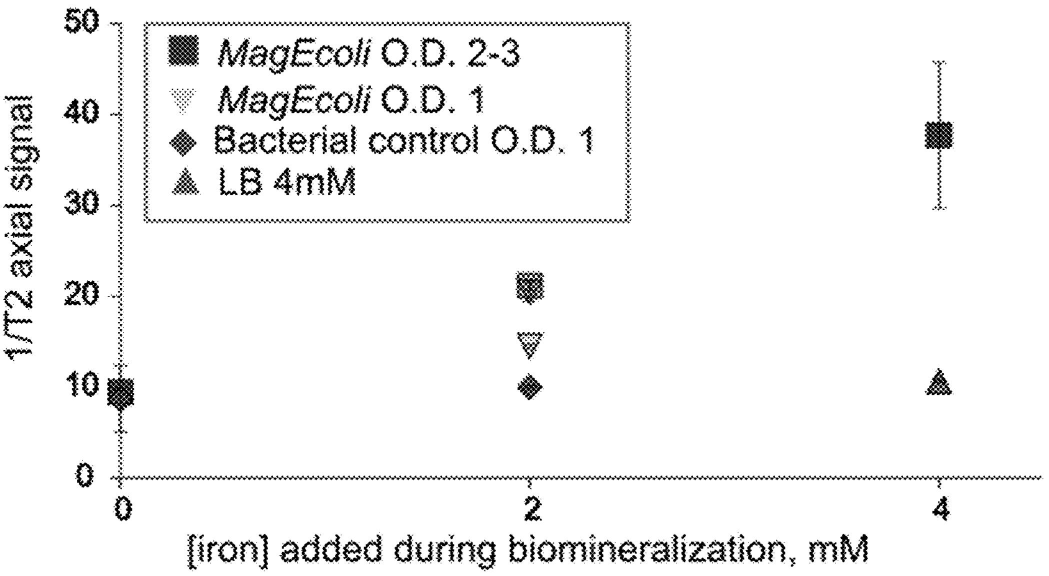

Next, the effect of iron concentration during mineralization towards the relaxation times was studied. The R2 of MagEcoli mineralized at 0, 2 and 4 mM for an optical density of 2-3 was measured inside the NMR tube. T2 decreases when the concentration of iron raises (FIG. 26B). Measures were also performed with 2 mM iron, at an O.D. of around 1 in the tube and it was observed that the effect of T2 was similar or slightly inferior as compared to 2-time concentrated MagEcoli (O.D. of 2-3). This might indicate that bacterial concentration in the tube may not have a strong impact as the impact of iron concentration. As a control, the R2 was measured for bacteria that did not over-express ferritin but that followed the same protocol of mineralization with 0 or 2 mM of iron. They were at an O.D. of 1 in the tube. For the control at 0 mM of iron, the T2 was the same for non-mineralized MagEcoli, as expected. For 2 mM of iron, the R2 did not increase significantly and it was inferior to the ones measured for MagEcoli at 2 mM of iron, at the same O.D. An additional measurement with LB supplemented with 4 mM of iron gave an R2 in the same range as the bacterial control. Altogether, these data indicate that MagEcoli have a distinct magnetic signature that have an impact on the relaxation times T2.

Figure 26C:
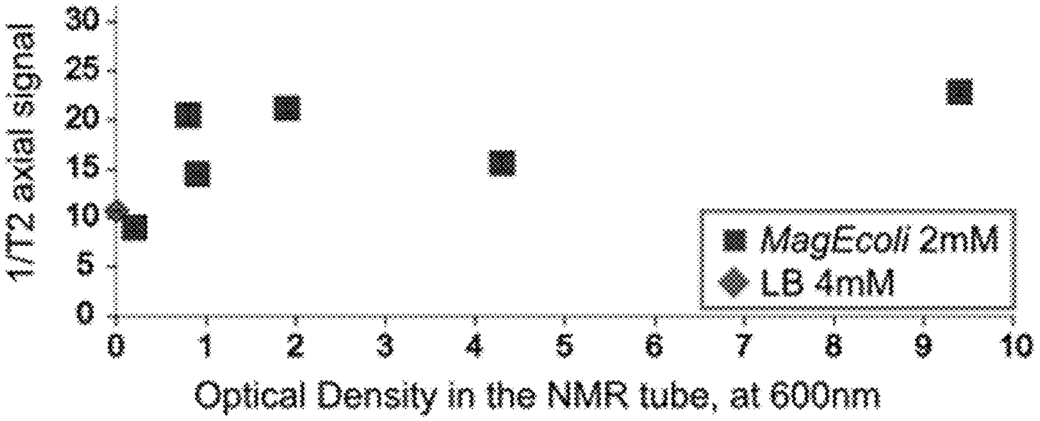

Then, the impact of bacterial concentration on the signal was assessed. For this purpose, different samples of MagEcoli mineralized at 2 mM of iron mixed in M9-agar at various O.D. were prepared. The data are displayed in FIG. 26C. We can see that for low O.D., 0.2, the signal is weaker and similar to the control (LB with 4 mM of iron): the R2 has a value around 10. However, when bacteria are more numerous in the tube, from O.D. around 1, the R2 clearly increases.

Finally, to confirm the potential use of 4 mM of iron-mineralized MagEcoli as contrast agent, a sample was prepared in which the MagEcoli were not homogeneously distributed. The idea was to see whether the regions enriched in bacteria could be distinguished from the rest of the sample. It was observed a difference of 1/T2 intensity for the coronal section, the diffusion streaks generated by the bacteria quickly entrapped in the M9-agar. These experimental data strongly suggest that magnetic bacteria according to the invention, i.e. MagEcoli, may be used as a negative contrast agent in vitro.

Example 3

The iron cellular content of biomineralized MagEcoli with 2 mM or 4 mM iron has been assessed following the protocols disclosed in "Standard Methods for Water and Wastewater Analysis", APHA 1992, as based on phenanthroline absorption. In addition, the number of iron atoms may be evaluated at the nanocage level (expressed in iron atoms per 24 ferritins or ferritin subunits).

Results are depicted in Table 3 below:

TABLE 3

| Concentration of iron added in the biomineralization medium | Cellular concentration of iron upon biomineralization | Number of iron atoms per nanocage (24 ferritins) |
|---|---|---|
| 0 mM | Below the detection threshold | — |
| 2 mM | 2 mM | 1,000 |
| 4 mM | 3 mM | 1,500 |

As seen in Table 3, the intracellular concentration of iron upon mineralization is high, and mainly accounts for a high level of iron atom per nanocage.

Example 4: Comparative Example

A biomineralization assay was performed as disclosed in example 1, 15 with 100 μM (comparative assay) and 2 mM ironII (invention's assay) (Mohr's salt). 100 μM ironII is a condition comparable with the amount of iron used in the literature (see, e.g., Garcia-Prieto et al., *Nanoscale,* 2016, vol. 8(2):1088-1099; Hill et al., PLOS One, 2011, vol. 6(10):e25409)

Figure 27:
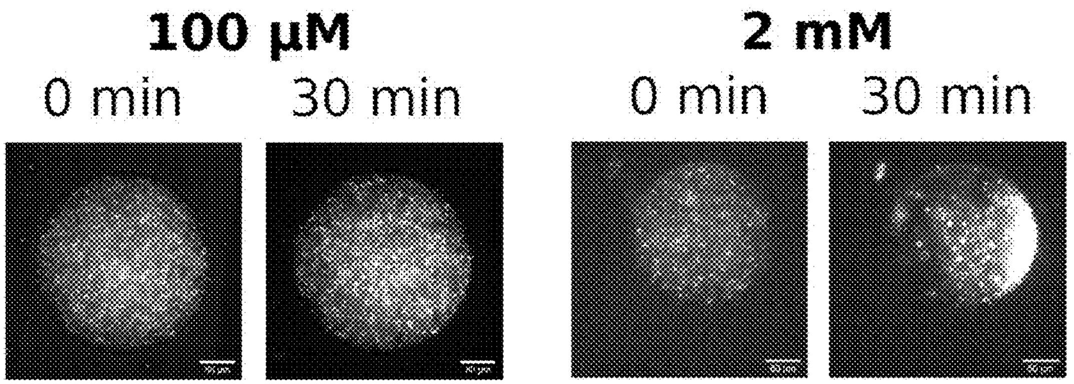
FIG. 27 represents photographs illustrating the time lapse images of MagEcoli bacteria biomineralized with 100 μM (left panels) or 2 mM (right panels) of iron II, 0 min and 30 min upon contact with a magnet (on the right). mCherry channel. Scale bar, 60 μM.

As seen in FIG. 27, bacteria mineralized with 100 μM iron are not attracted by the magnet after 30 min (left panels), whereas bacteria mineralized with 2 mM iron are attracted by the magnet (right panels). The analysis of the trajectories of bacteria in each condition shows that they are linear and oriented towards the magnet for the bacteria mineralized with 2 mM iron, and aleatory for the bacteria mineralized with 100 μM iron (illustrative of the brownian movement of bacteria).

Sequences Used Herein

| SEQ ID NO: | Sequence | Description |
|---|---|---|
| 1 | MLSERMLKALNDQLNRELYSAYLYFAMAAYFEDL GLEGFANWMKAQAEEEIGHALRFYNYIYDRNGRV ELDEIPKPPKEWESPLKAFEAAYEHEKFISKSIY ELAALAEEEKDYSTRAFLEWFINEQVEEEASVKK ILDKLKFAKDSPQILFMLDKELSARAPKLPGLLM QGGE | Amino acid sequence of the ferritin of *P. furiosus* |
| 2 | atgttgagcgaaagaatgctcaaggctttaaatg accagctaaacagggagctttattctgcatatct atactttgccatggctgcctactttgaagatctt ggccttgaaggtttcgccaactggatgaaggctc aggctgaagaagagattgggcatgcactgaggtt ctacaactacatctacgatcgcaatggtagggtt gagcttgatgaaattccaaagcctccaaaggagt gggagagcccattaaaagcttttgaagctgctta cgagcatgagaaattcataagcaagtccatatat gaattggcagctttagcagaggaggaaaaagatt actcgacgagggcattctagagtggtttatcaac gagcaggttgaggaagaggccagcgtaaagaaaa tactggacaagttaaagtttgctaaggacagtcc tcaaatattgttcatgcttgataaggagttgagt gcgagagctccaaagctcccagggctcttaatgc agggaggagagtaa | Nucleic acid sequence of the ferritin of *P. furiosus* |

The invention claimed is:

1. A recombinant, alive and metabolically active magnetic bacterium comprising a heterologous prokaryotic biomineralized ferritin, wherein said ferritin is originating from an archaeon of the genus *Pyrococcus* and is structured as a nanocage, wherein said nanocage has an external diameter from about 12 nm to about 16 nm, and wherein said bacterium transmits its magnetic properties through cell division via asymmetrical transmission of iron oxides ferritin-enriched bodies to daughter cells.

2. The bacterium according to claim 1, wherein said bacterium is of the genus *Escherichia.*

3. The bacterium according to claim 1, wherein said bacterium is of the species *E. coli.*

4. The bacterium according to claim 1, wherein said ferritin is originated from an archaeon of the species *Pyrococcus furiosus.*

5. The bacterium according to claim 1, wherein said nanocages form inclusion bodies within the producing recombinant bacterium.

6. The bacterium according to claim 1, wherein the bacterium is of the species *E. coli*, the ferritin is originating from an archaeon of the species *Pyrococcus furiosus*, and the nanocage comprises at least about 1000 iron atoms.

7. A method for detecting and/or capturing of one or more target chemical substance(s) and/or one or more organism(s) comprising providing as a biosensor the recombinant bacterium according to claim 1.

8. A method of screening, comprising providing the bacterium according to claim 1 for the surface display of a ligand.

9. A method to treat and/or prevent a disease comprising the administration of a therapeutically effective amount of a recombinant bacterium according to claim 1.

10. The method to treat and/or prevent a disease according to claim 9, wherein the recombinant bacterium is used as a molecule delivery system.

11. The method to treat and/or prevent a disease according to claim 9, wherein the recombinant bacterium is used for the surface display of a protein of interest that recognizes and/or penetrates a target cell.

12. The method to treat and/or prevent a disease according to claim 9, wherein the recombinant bacterium is used for the surface display of a protein of interest that recognizes and/or penetrates a mammal target cell.

13. The method to treat and/or prevent a disease according to claim 9, wherein the recombinant bacterium is used for the surface display of a protein of interest that recognizes and/or penetrates a human target cell.

14. A method for diagnosing a disorder, said method comprising the steps of: (a) contacting bacteria according to claim 1 with a sample collected from an individual as to allow the interaction of a biomarker specific to said disorder by said bacteria; (b) applying a magnetic field to concentrate and/or sort the bacteria; and (c) detecting a signal resulting from the interaction of said biomarker by said bacteria, wherein the said detection of a signal is indicative of the occurrence in a disorder in said individual.

* * * * *

SEQUENCE LISTING

```
<160> NUMBER OF SEQ ID NOS: 2

<210> SEQ ID NO 1
<211> LENGTH: 174
<212> TYPE: PRT
<213> ORGANISM: Pyrococcus furiosus
<220> FEATURE:
<223> OTHER INFORMATION: Amino acid sequence of the ferritin of P.
      furiosus

<400> SEQUENCE: 1

Met Leu Ser Glu Arg Met Leu Lys Ala Leu Asn Asp Gln Leu Asn Arg
1               5                   10                  15

Glu Leu Tyr Ser Ala Tyr Leu Tyr Phe Ala Met Ala Ala Tyr Phe Glu
            20                  25                  30
```

-continued

```
Asp Leu Gly Leu Glu Gly Phe Ala Asn Trp Met Lys Ala Gln Ala Glu
        35                  40                  45

Glu Glu Ile Gly His Ala Leu Arg Phe Tyr Asn Tyr Ile Tyr Asp Arg
    50                  55                  60

Asn Gly Arg Val Glu Leu Asp Glu Ile Pro Lys Pro Pro Lys Glu Trp
65                  70                  75                  80

Glu Ser Pro Leu Lys Ala Phe Glu Ala Ala Tyr Glu His Glu Lys Phe
                85                  90                  95

Ile Ser Lys Ser Ile Tyr Glu Leu Ala Ala Leu Ala Glu Glu Glu Lys
            100                 105                 110

Asp Tyr Ser Thr Arg Ala Phe Leu Glu Trp Phe Ile Asn Glu Gln Val
        115                 120                 125

Glu Glu Glu Ala Ser Val Lys Lys Ile Leu Asp Lys Leu Lys Phe Ala
    130                 135                 140

Lys Asp Ser Pro Gln Ile Leu Phe Met Leu Asp Lys Glu Leu Ser Ala
145                 150                 155                 160

Arg Ala Pro Lys Leu Pro Gly Leu Leu Met Gln Gly Gly Glu
                165                 170


<210> SEQ ID NO 2
<211> LENGTH: 525
<212> TYPE: DNA
<213> ORGANISM: Pyrococcus furiosus
<220> FEATURE:
<223> OTHER INFORMATION: Nucleic acid sequence of the ferritin of P.
      furiosus

<400> SEQUENCE: 2

atgttgagcg aaagaatgct caaggcttta aatgaccagc taaacaggga gctttattct      60

gcatatctat actttgccat ggctgcctac tttgaagatc ttggccttga aggtttcgcc     120

aactggatga aggctcaggc tgaagaagag attgggcatg cactgaggtt ctacaactac     180

atctacgatc gcaatggtag ggttgagctt gatgaaattc caaagcctcc aaaggagtgg     240

gagagcccat taaaagcttt tgaagctgct tacgagcatg agaaattcat aagcaagtcc     300

atatatgaat tggcagcttt agcagaggag gaaaaagatt actcgacgag ggcattctta     360

gagtggttta tcaacgagca ggttgaggaa gaggccagcg taaagaaaat actggacaag     420

ttaaagtttg ctaaggacag tcctcaaata ttgttcatgc ttgataagga gttgagtgcg     480

agagctccaa agctcccagg gctcttaatg cagggaggag agtaa                     525
```